(12) United States Patent
Nishikawa et al.

(10) Patent No.: US 8,351,029 B2
(45) Date of Patent: Jan. 8, 2013

(54) OPTICAL FIBER SENSOR

(75) Inventors: Satoshi Nishikawa, Tokyo (JP);
Masakazu Takabayashi, Tokyo (JP);
Eiji Yagyu, Tokyo (JP); Kiichi Yoshiara, Tokyo (JP); Tateki Mitani, Tokyo (JP);
Yutarou Hamatani, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 280 days.

(21) Appl. No.: 12/745,815

(22) PCT Filed: Dec. 3, 2008

(86) PCT No.: PCT/JP2008/003568
§ 371 (c)(1),
(2), (4) Date: Jun. 2, 2010

(87) PCT Pub. No.: WO2009/072274
PCT Pub. Date: Jun. 11, 2009

(65) Prior Publication Data
US 2010/0296080 A1 Nov. 25, 2010

(30) Foreign Application Priority Data
Dec. 6, 2007 (JP) ................................. 2007-316084

(51) Int. Cl.
*G01N 21/41* (2006.01)
*G01J 1/00* (2006.01)
(52) U.S. Cl. ........................................ 356/128; 356/213
(58) Field of Classification Search .................. 356/128
See application file for complete search history.

(56) References Cited

U.S. PATENT DOCUMENTS 6,895,132 B2 * 5/2005 Moslehi et al. ................. 385/13
7,672,544 B2 * 3/2010 Takabayashi et al. .......... 385/12
(Continued)

FOREIGN PATENT DOCUMENTS
JP        1 282449        11/1989
(Continued)

OTHER PUBLICATIONS

Chinese Office Action issued Aug. 30, 2011, in Patent Application No. 200880119063.1 (with English-language translation).

(Continued)

*Primary Examiner* — Michael P Stafira
(74) *Attorney, Agent, or Firm* — Oblon, Spivak, McClelland, Maier & Neustadt, L.L.P.

(57) ABSTRACT

An objective of the present invention is to provide an optical fiber sensor which has a simple configuration to enable sensitively measuring a refractive index of a measurement medium in a wide range of refractive indexes. An optical fiber sensor according to the present invention includes; an optical fiber having a core in which a short-period gratings are formed and a cladding, the optical fiber being made so that transmission loss occurs due to cladding-propagation-mode leakage at its cladding portion where the short-period gratings are formed; a light source from which light having a wavelength range of the cladding propagation mode is emitted; and a light receiving unit for receiving transmission or reflection light having passed through the cladding at the position where the short-period gratings are formed. The optical fiber sensor detects, based on the total receiving light intensity that the light receiving unit receives, the refractive index of the measurement medium contacting the cladding, in which the optical fiber is multi-mode one, and the short-period gratings have plural kinds of periods.

15 Claims, 24 Drawing Sheets

U.S. PATENT DOCUMENTS

| | | |
|---|---|---|
| 2005/0269490 A1 | 12/2005 | Loock et al. |
| 2007/0075225 A1 | 4/2007 | Xia et al. |
| 2009/0034901 A1 | 2/2009 | Takabayashi et al. |
| 2010/0080502 A1 | 4/2010 | Nishikawa et al. |

FOREIGN PATENT DOCUMENTS

| | | |
|---|---|---|
| JP | 2003 194635 | 7/2003 |
| JP | 2007 101547 | 4/2007 |
| WO | 02 44697 | 6/2002 |
| WO | 2005 119212 | 12/2005 |
| WO | 2006 126468 | 11/2006 |
| WO | 2008 111320 | 9/2008 |

OTHER PUBLICATIONS

Zhao, Chun-Liu et al., "Simultaneous Temperature and Refractive Index Measurements Using a 3° Slanted Multimode Fiber Bragg Grating", Journal of Lighwave Technology, vol. 24, No. 2, pp. 879-883, (Feb. 2006).

* cited by examiner

OPTICAL FIBER SENSOR

TECHNICAL FIELD

The present invention relates to an optical fiber sensor, especially relates to an optical fiber sensor for detecting liquid characteristics by utilizing a refractive index.

BACKGROUND ART

Pure gasoline used as automobile-engine fuel includes light gasoline including a hydrocarbon, as a main component, such as heptane and pentane, heavy gasoline including that, as a main component, such as benzene, and their intermediate medium gasoline (normal regular gasoline); therefore, if an ignition timing, etc., is not dully controlled corresponding to the characteristics of the gasoline, deterioration of driving performance or increase of harmful components included in the exhaust gas will occur.

In the USA and in European countries, in order to reduce the amount of petroleum oil consumption, fuel of gasoline mixed with alcohol becomes popular for automobiles, so that, by controlling the air-fuel ratio and the ignition timing corresponding to the alcohol content of the fuel, the air-fuel-ratio leaning can be prevented.

For a method of detecting characteristics of such fuel, a sensor being a type of measuring the refractive index of the fuel has been developed.

For example, a liquid-characteristics detection sensor has been disclosed in which, by inputting light from a light source into a short-period tilted grating, variation of a transmission-spectrum envelope shape fluctuating in accordance with a refractive index of material surrounding the grating under a cladding propagation mode, is analyzed using a signal analyzer (for example, Patent Document 1).

Further a liquid-characteristics detection sensor has been disclosed in which, by inputting light from a light source into a single short-period grating, variation of a transmission-spectrum shape fluctuating in accordance with a reflective index of material surrounding the grating under a cladding propagation mode is measured as a change in total receiving-light-amount, to thereby detect the reflective index (for example, Patent Document 2).

[Patent Document 1] International Publication WO 02/44697 (page 12 to 26, FIG. 3)

[Patent Document 2] International Publication WO 2006/126468 (page 6 to 9, FIG. 1)

DISCLOSURE OF THE INVENTION

Problems to be Solved by the Invention

However, in the detection method using the short-period tilted grating as disclosed in Patent Document 1, because the spectrum shape of loss peaks under a cladding-propagation-mode is needed to be measured in a higher wavelength resolution, an expensive measurement apparatus such as an optical spectrum analyzer is necessary; therefore, it has been difficult to measure the refractive index only by simply detecting the light intensity thereof.

Moreover, in the method of detecting the variation of the detection light intensity using the single short-period grating as disclosed in Patent Document 2, in order to obtain a wide refractive-index measurement range, a core diameter of the optical fiber is needed to be decreased; as a result, a case has occurred that the light emission of the light source such as an LED cannot necessarily be effectively used. In contrast, when the core diameter of the optical fiber is increased, because a wavelength range where the transmittance varies with the refractive index of a target to be measured is narrowed, the ratio of the variation amount of the light detection intensity to the total light detection intensity may be decreased; as a result, a case has occurred that sufficient measurement sensitivity cannot necessarily be obtained.

An objective of the present invention, which is made to solve the above described problem, is to provide an optical fiber sensor which has a simple configuration to enable sensitively measuring a refractive index of a measuring target in a wide range of refractive indexes.

Means for Solving the Problems

An optical fiber sensor according to the present invention includes a light source, an optical fiber including a core having a plurality of short-period gratings whose periods are different from each other, and a cladding for covering the core, and a light receiving unit for detecting an intensity of light that has been inputted into the optical fiber from the light source and passed through the short-period gratings.

According to the present invention, a variation amount of the received light intensity can be increased relative to a refractive-index fluctuation of the target, so that the sensitivity of the sensor can be increased.

EXPLANATION OF REFERENCES

1: Optical fiber, 2: Light source, 3: Light receiving unit, 4: Core, 5: Cladding, 6: Fiber jacket, 8: Target to be measured, 9: Container, 10, 11, 12: Short-period grating, 20: Circulator, 21: Reflection grating, 30: Beam, 31: Medium, 32: Container, 40: Thermometer, 41: Characteristic calculation unit, 50: Characteristic calculation unit, 80, 90: Signal line, 100: Central axis of optical fiber, 101: Line, crossing central axis of optical fiber, among refractive index periodically-varying axes. 200: Transmission loss peak, 201: Envelope

BEST MODE FOR CARRYING OUT THE INVENTION

Embodiment 1

Figure 1:
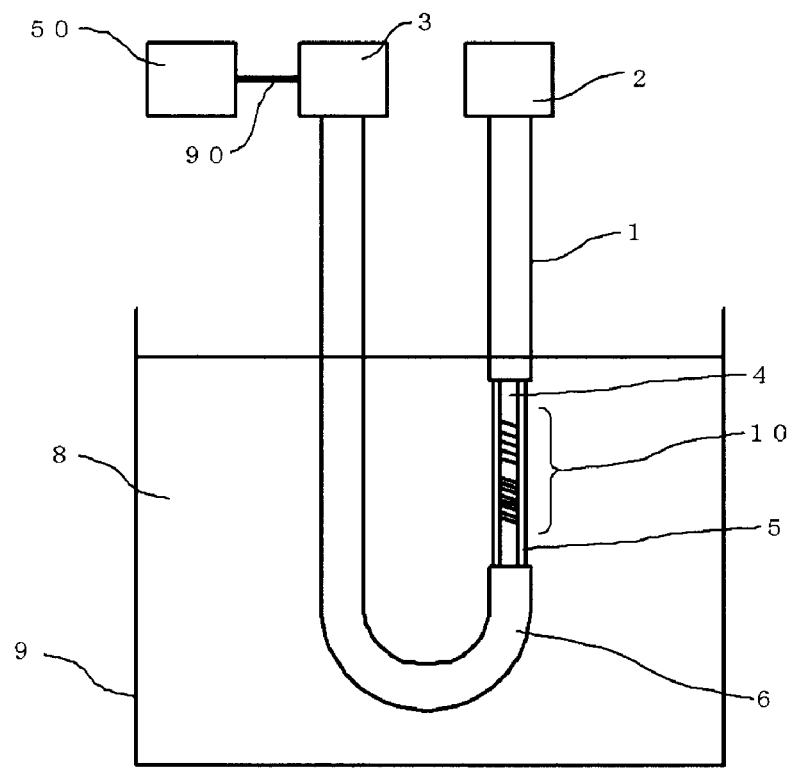
FIG. 1 is a schematic view explaining an optical fiber sensor according to Embodiment 1 of the present invention.

FIG. 1 is a schematic diagram explaining an optical fiber sensor according to Embodiment 1 implementing the present invention. In FIG. 1, a light source 2 is arranged at one end portion of an optical fiber 1, and a light receiving unit 3 is arranged at the other end portion. The optical fiber 1 is provided with a core 4 through which light mainly from the light source 2 propagates, a cladding 5 covering the core 4 so that light is confined in the core 4, and a fiber jacket 6 which covers and protects the cladding 5. A part of the fiber jacket 6 is removed so that the cladding 5 directly contacts a liquid target 8 to be measured, and short-period gratings 10 are formed on the core 4 corresponding to the portion from which the fiber jacket 6 is removed. The optical fiber sensor is configured with the optical fiber 1, the light source 2, the light receiving unit 3, and a refractive-index calculation unit 50 connected to the light receiving unit 3 through a signal line 90. The optical fiber 1 is arranged bent in a U-shape in the proximity of the bottom of a container 9 in which the target 8 is stored, while the light source 2 and the light receiving unit 3 are arranged exterior of the container 9.

Here, for example, a light emitting diode (LED) is used as the light source 2, a photodiode is used as the light receiving unit 3, and a quarts multimode optical fiber of a germanium (Ge)-added core, being graded-index type is used as the optical fiber 1 in which acrylic resin is used as the fiber jacket 6, the diameter of the core 4 is 62.5 micro-m, and that of the cladding 5 is 125 micro-m.

Figure 2:
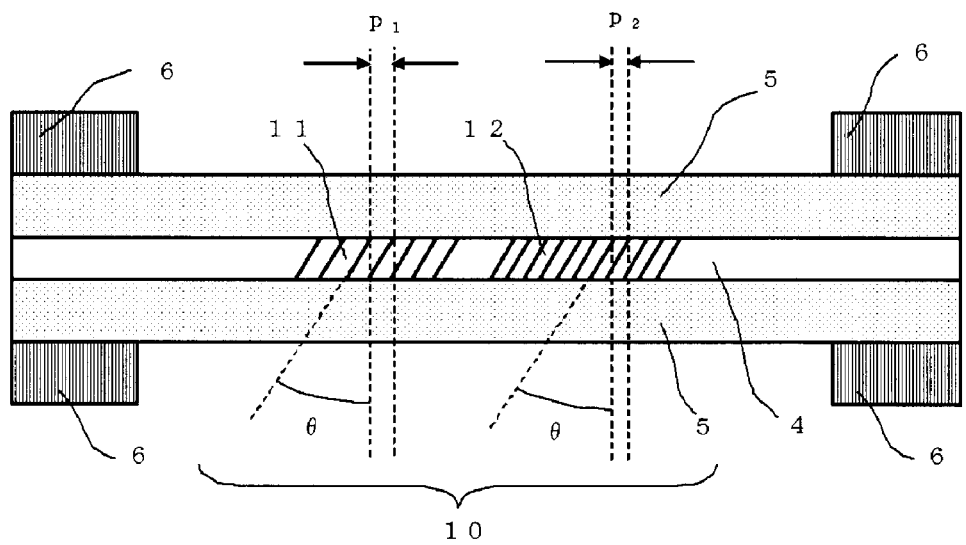
FIG. 2 is a cross-sectional schematic view of a region where short-period gratings of the optical fiber sensor according to Embodiment 1 of the present invention are formed.

FIG. 2 is a schematic diagram in which a region where the short-period gratings 10 of the optical fiber sensor in FIG. 1 are formed is magnified and represented. In FIG. 2, a first short-period grating 11 having a first period p1 and a second short-period grating 12 having a second period p2 are provided to be spaced apart from each other in the core 4. The first period p1 and the second period p2 are different from each other, and the first short-period grating 11 and the second short-period grating 12 each have a tilt angle of an angle theta.

In the optical fiber sensor according to this embodiment, the first short-period grating 11 having the first period p1 of 0.3 micro-m and the second short-period grating 12 having the second period p2 of 0.294 micro-m are formed, as illustrated in FIG. 2, with their tilt angle theta being 8.6 degrees, in a range of 10 mm of the length of the optical fiber 1.

Figure 3:
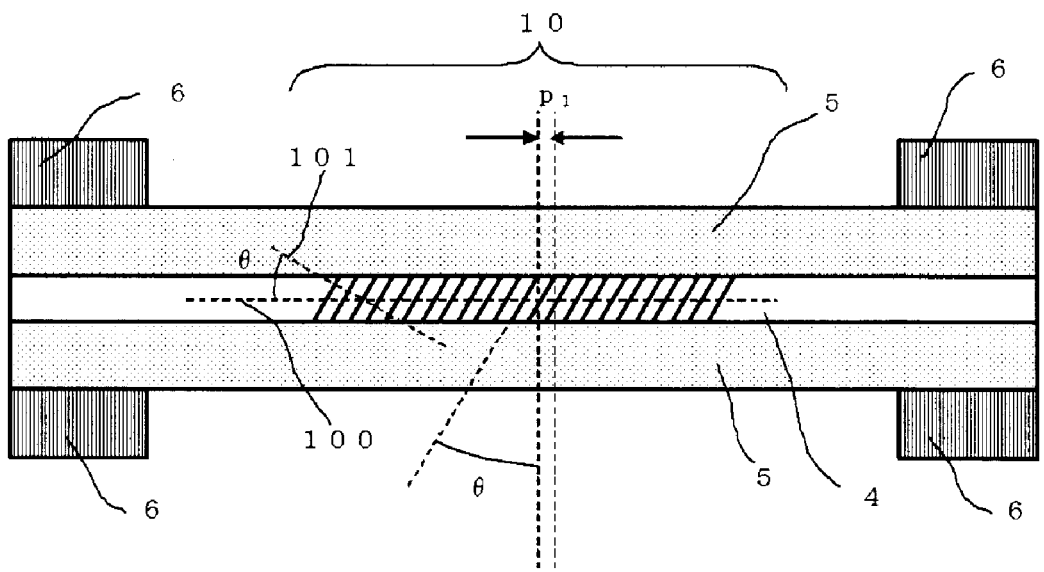
FIG. 3 is a cross-sectional schematic view explaining a region where the a short-period grating of the optical fiber sensor according to Embodiment 1 of the present invention are formed.

Here, the period and the tilt angle of the short-period gratings 10 are explained using FIG. 3 which is a schematic view illustrating a region where the short-period gratings 10 are formed to be tilted. In FIG. 3, the refractive index of the core 4 periodically varies in the portion of the short-period gratings 10, and the varying period p1 of the refractive index in a direction of a central axis 100 of the optical fiber 1 is referred to as a "period". Additionally, the angle theta between a line 101, crossing the central axis of optical fiber 1, among refractive index periodically-varying axes and the central axis 100 of the optical fiber 1, is referred to as a "tilt angle".

Here, the tilt angle is given to be larger than – (minus) 90 degrees and smaller than 90 degrees.

Next, an operation of the optical fiber sensor according to this embodiment, as well as an effect of providing the short-period gratings 10 having a plurality of periods are explained using FIG. 1 to FIG. 5

When near-infrared light emitted from the LED as the light source 2 reaches the short-period gratings 10 of the optical fiber 1, periodical sharp transmission loss peaks referred to as a cladding propagation mode generate within a specific wavelength range with respect to the transmission spectrum of the optical fiber 1. As the refractive index of the target 8, to be measured, that contacts the outer periphery of the cladding 5 in the region where the short-period gratings 10 are provided, comes close to that of the cladding 5, the transmission loss peaks under this cladding propagation mode are likely to be vanished from the short wavelength side thereof, and finally changes into a continuous loss-spectrum shape of little wavelength-dependence. Depending on the degree of occurrence of transmission-loss-peaks under the cladding propagation mode, light intensity reaching the light receiving unit 3 connected to the optical fiber 1 varies; therefore, by previously determining a relationship between the received light intensities and the refractive indexes, the refractive index of the target to be measured can be outputted from the refractive-index calculation unit 50 to which the intensity of the light reaching the light receiving unit 2 is inputted through a signal line 90.

In addition, with the thus measured refractive index of the target 8, the characteristics of the target 8, such as mixing ratio of gasoline and alcohol, can be measured, by previously determining a relationship between the refractive indexes and the properties of the target 8.

Figure 4:
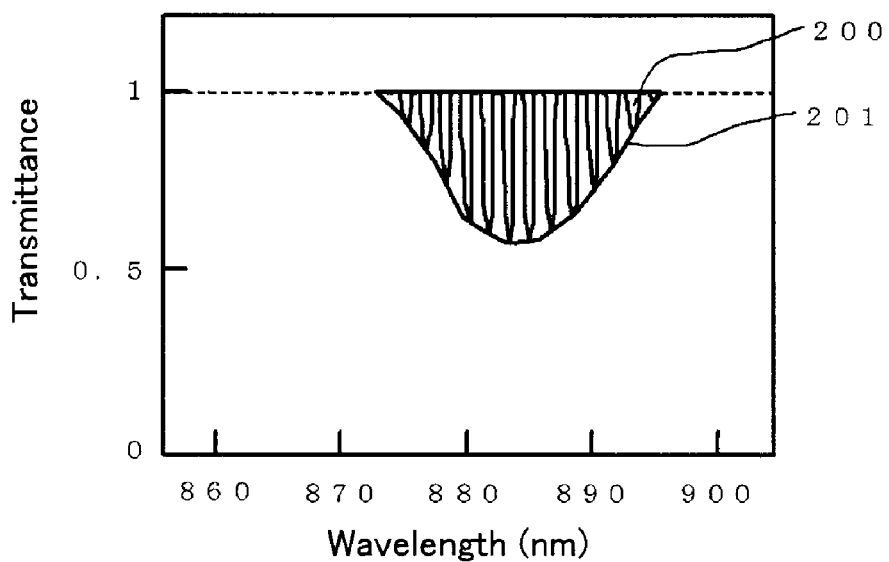
FIG. 4 is a schematic graph of a transmittance of an optical fiber of the optical fiber sensor according to Embodiment 1 of the present invention.

As represented in FIG. 3, when the optical fiber sensor has a short-period grating 10 having a single period, in which the period is 0.3 micro-m and the tilt angle is 8.6 degrees, the transmission spectrum of the optical fiber 1 is represented as in FIG. 4, in which an envelope 201 of cladding-propagation-mode transmission loss peaks 200 becomes a distribution shape whose center wavelength is 880 nm, and the wavelength range where the cladding propagation mode occurs becomes approximately 10 to 15 nm. In contrast, regarding the transmission light spectrum of the optical fiber 1, having two kinds of periods as represented in FIG. 2, of the optical fiber sensor according to this embodiment, the envelope 201 of the cladding-propagation-mode transmission loss peaks becomes a shape such that two similar distributions are lapped, and the wavelength range where the cladding propagation mode occurs is extended.

Figure 5:
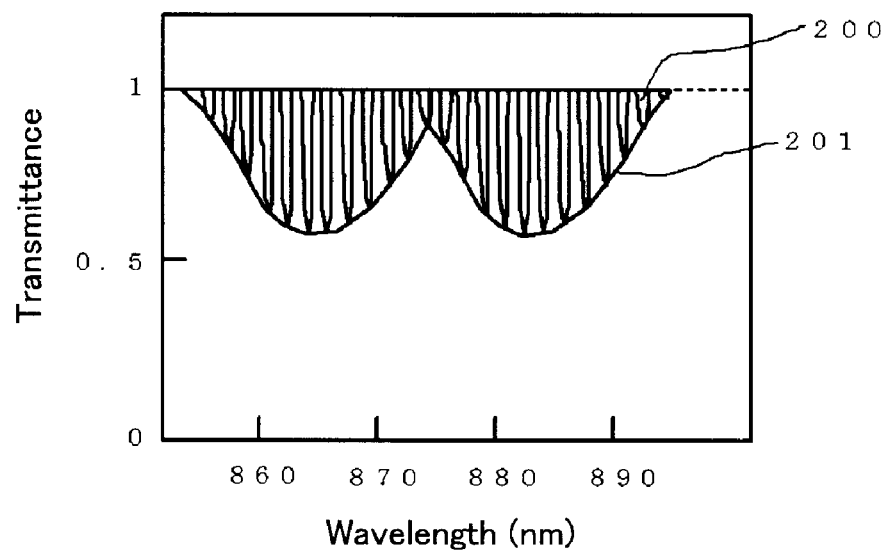
FIG. 5 is a schematic graph of a transmittance of the optical fiber of the optical fiber sensor according to Embodiment 1 of the present invention.

As described above, because the cladding-propagation-mode wavelengths vary in proportional to the period of the short-period grating, by using the optical fiber sensor provided with the short-period gratings, represented in FIG. 2, having the two kinds of periods, cladding propagation modes occur, as represented in FIG. 5, in two wavelength ranges which are determined depending on a proportional relationship of these periods and whose central wavelengths are shifted from each other, so that wavelength range in which cladding propagation mode occurs is extended up to approximately the double thereof.

Subsequently, operational temperature dependency of the optical fiber sensor according to this embodiment is explained by the following simulation, in which increase of the number of the period elements of the short-period gratings 10 makes to increase detection sensitivity of the sensor and reduce the temperature dependency thereof.

Figure 6:
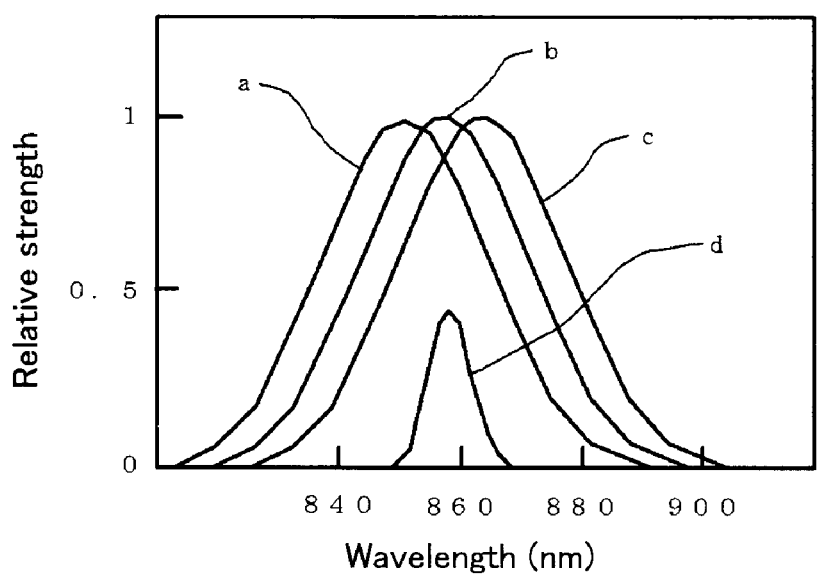
FIG. 6 is a schematic graph representing an absorption spectrum of the optical fiber and light emission spectra of a light source according to Embodiment 1 of the present invention.
Figure 7:
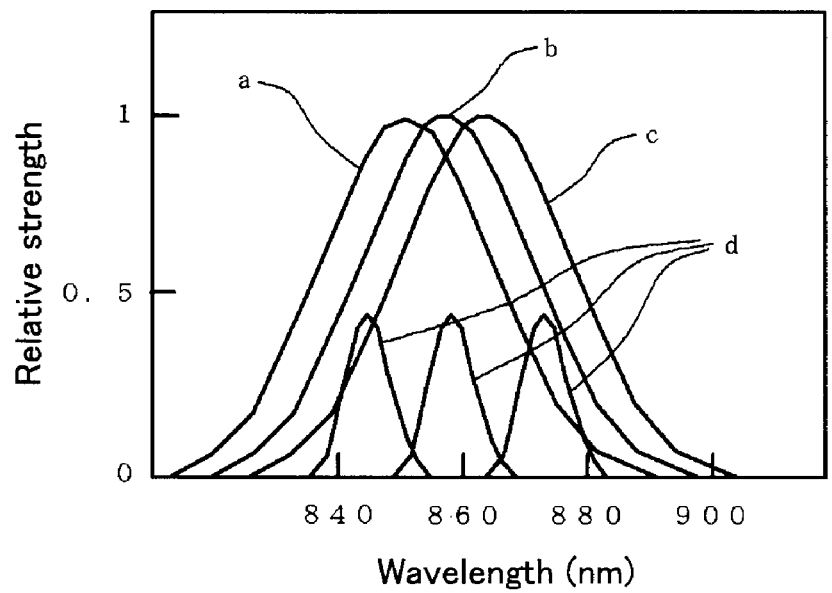
FIG. 7 is a schematic graph representing a relationship between absorption spectra of the optical fiber and the light emission spectra of the light source according to Embodiment 1 of the present invention.
Figure 8:
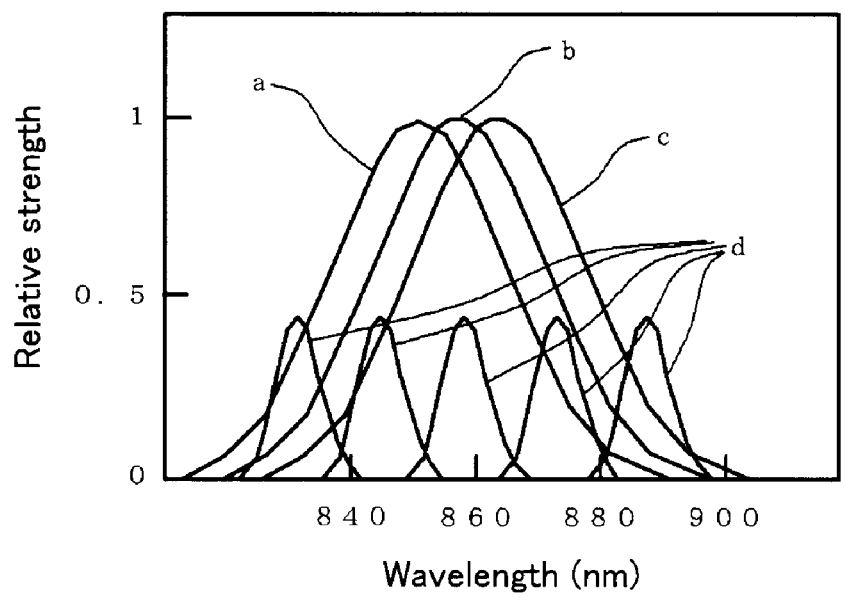
FIG. 8 is a schematic graph representing absorption spectra of the optical fiber and the light emission spectra of the light source according to Embodiment 1 of the present invention.

FIG. 6, FIG. 7, and FIG. 8 are diagrams representing LED light emission spectra, and relative-strength spectra obtained by approximating by normal distribution curves the envelopes of the transmission loss peaks under cladding propagation mode, for respective cases of the periods of the short-period gratings 10 being one kind, three kinds and five kinds. In FIG. 6, FIG. 7, and FIG. 8, spectra a, b, and c are calculated by approximating by a temperature coefficient of the LED the spectra emitted from the light source 2 in respective cases of the temperatures of 27 degrees, 48.5 degrees, and 70 degrees, and spectra d are the envelopes of the transmission loss peaks under the cladding propagation mode of the respective short-period gratings 10. The LED is set so that the light intensities incident on the respective short-period gratings 10 are the same. Here, no attention is given to the temperature dependency of the cladding propagation mode of the short-period gratings 10, because the dependency is less than that of the LED light emission spectrum by one order or more of magnitude. The period of the short-period gratings 10 is set to be 0.292 micro-m, the tilt angle thereof is to be 8.6 degrees, and the peak wavelengths of b and d are set to be identical to each other.

Here, with respect to the cladding-propagation-mode transmission loss corresponding to each kind of the periods, the following approximation is performed for simplifying the calculation. In longer wavelength side than that corresponding to the refractive index of the target 8 outside the cladding 5, periodical sharp transmission loss peaks of the cladding propagation mode are existent, and wavelength average transmission loss in proportional to the size represented by the transmission-loss-peak envelope is assumed to occur simultaneously for each kind of the periods. On the other hand, in shorter wavelength side than that corresponding to the refractive index of the target 8 outside the cladding 5, because the periodical sharp transmission loss peaks disappear and the wavelength average transmission loss increases, loss of the double of the transmission loss occurred in the longer wavelength side is assumed to occur.

Figure 9:
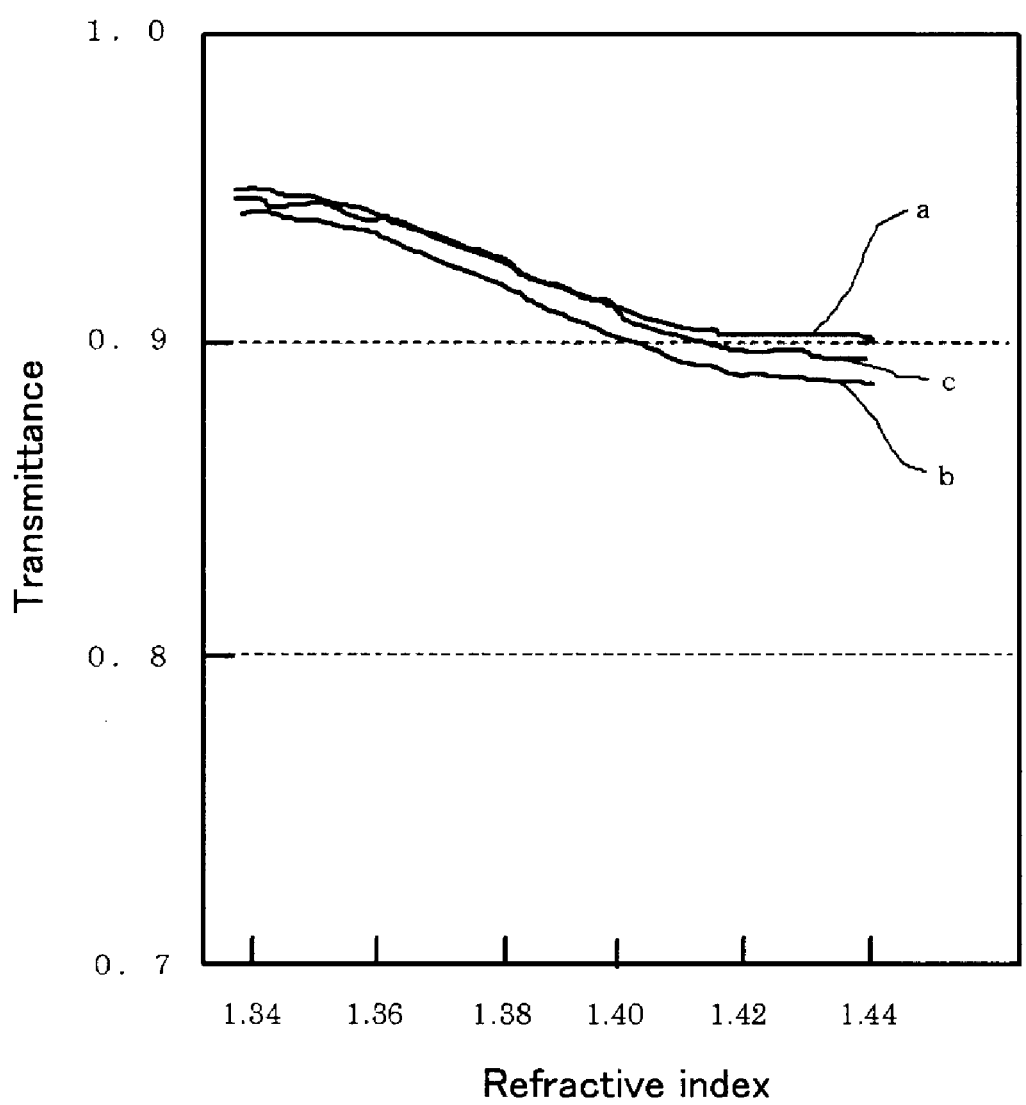
FIG. 9 is a graph representing input/output values of the optical fiber sensor according to Embodiment 1 of the present invention.
Figure 10:
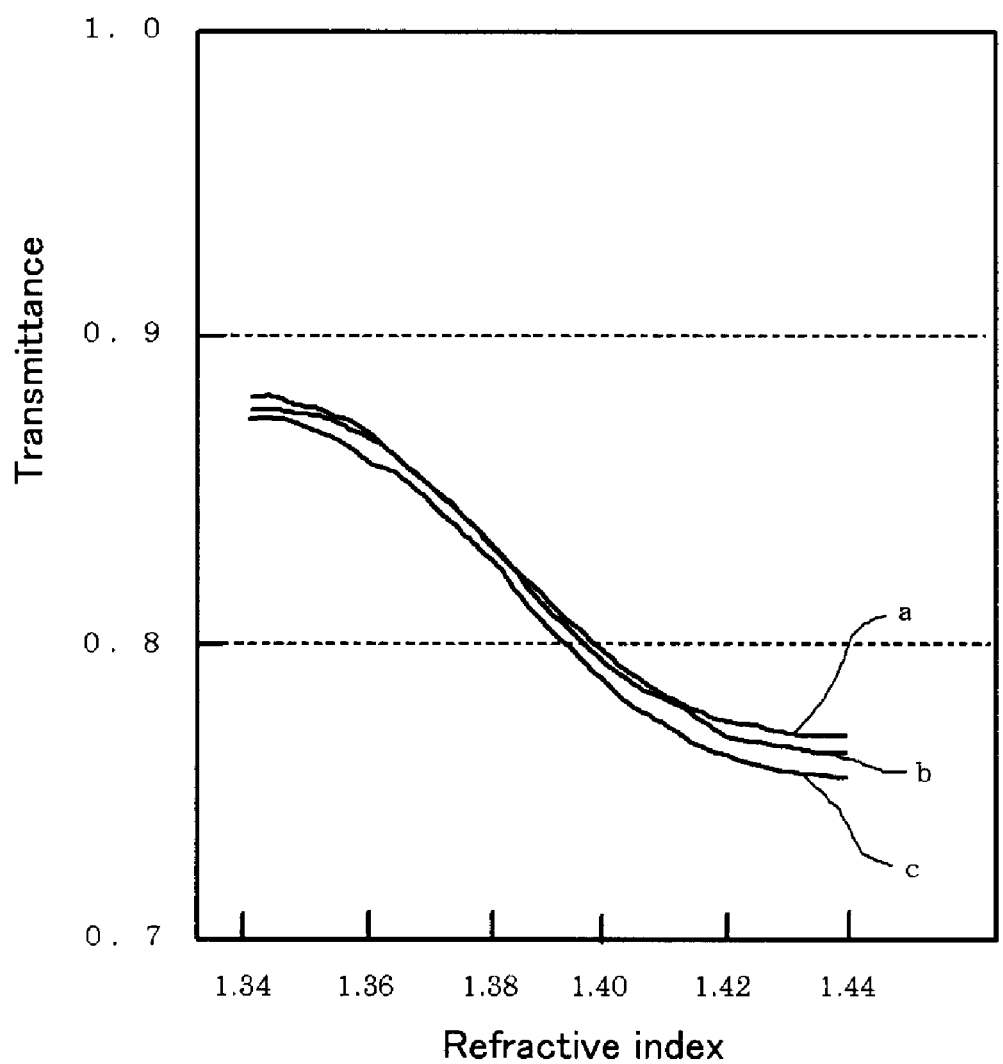
FIG. 10 is a graph representing input/output values of the optical fiber sensor according to Embodiment 1 of the present invention.
Figure 11:
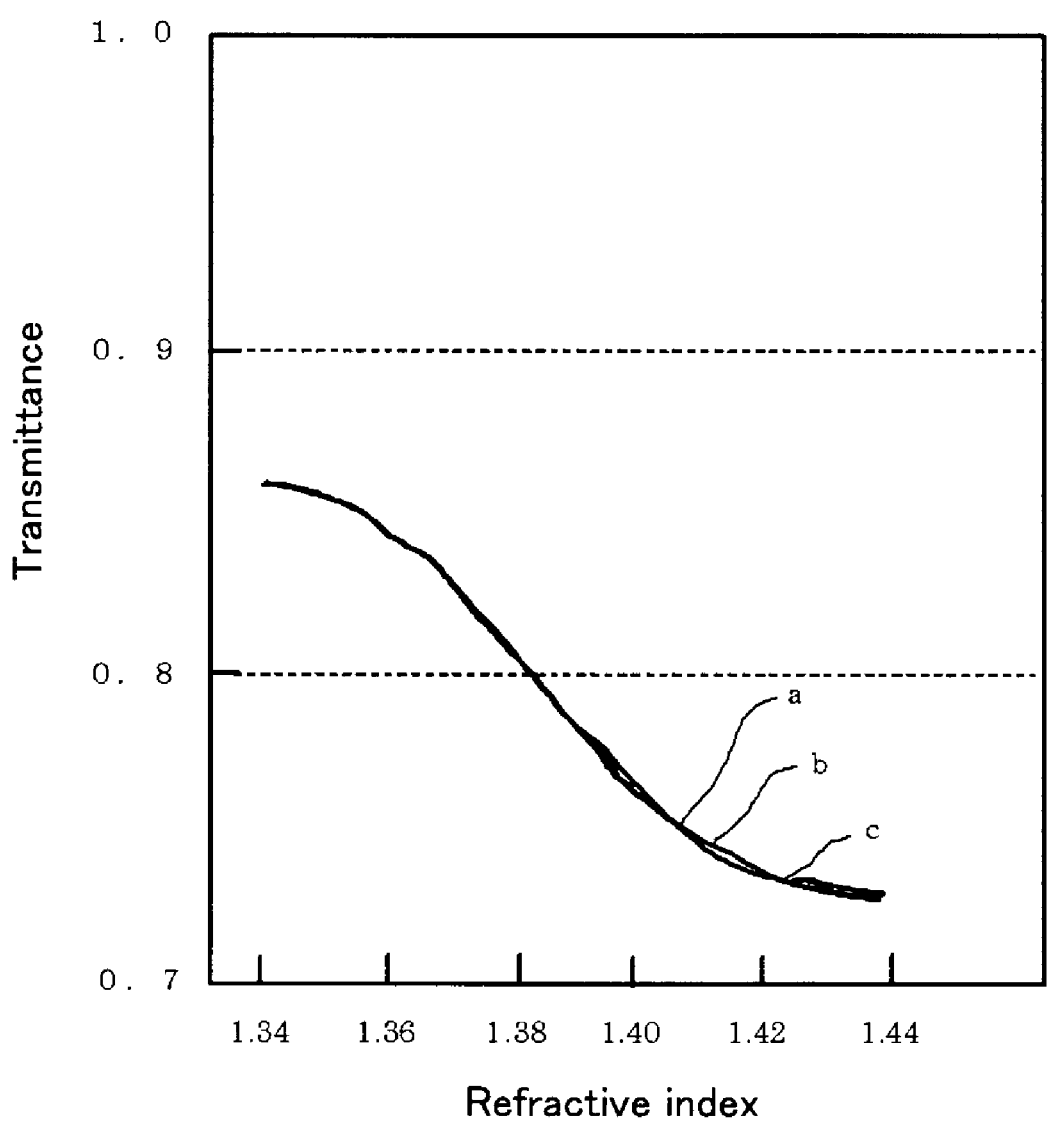
FIG. 11 is a graph representing input/output values of the optical fiber sensor according to Embodiment 1 of the present invention.

FIG. 9, FIG. 10, and FIG. 11 are resulted from the calculation by the above approximation, showing refractive-index dependency of the target 8, that is, a substance positioned outside the cladding 5 of a peeled portion of the fiber jacket 6, to the relative transmittance of the optical fiber 1, in respective cases of the periods of the short-period gratings 10 being one kind, three kinds and five kinds.

In FIG. 9, FIG. 10, and FIG. 11, symbols a, b and c denote the refractive-index dependency of the transmittance at temperatures of 27 degrees, 48.5 degrees and 70 degrees, respectively. Here, the shorter-wavelength-side cladding propagation mode corresponds to a lower refractive-index-side.

Figure 12:
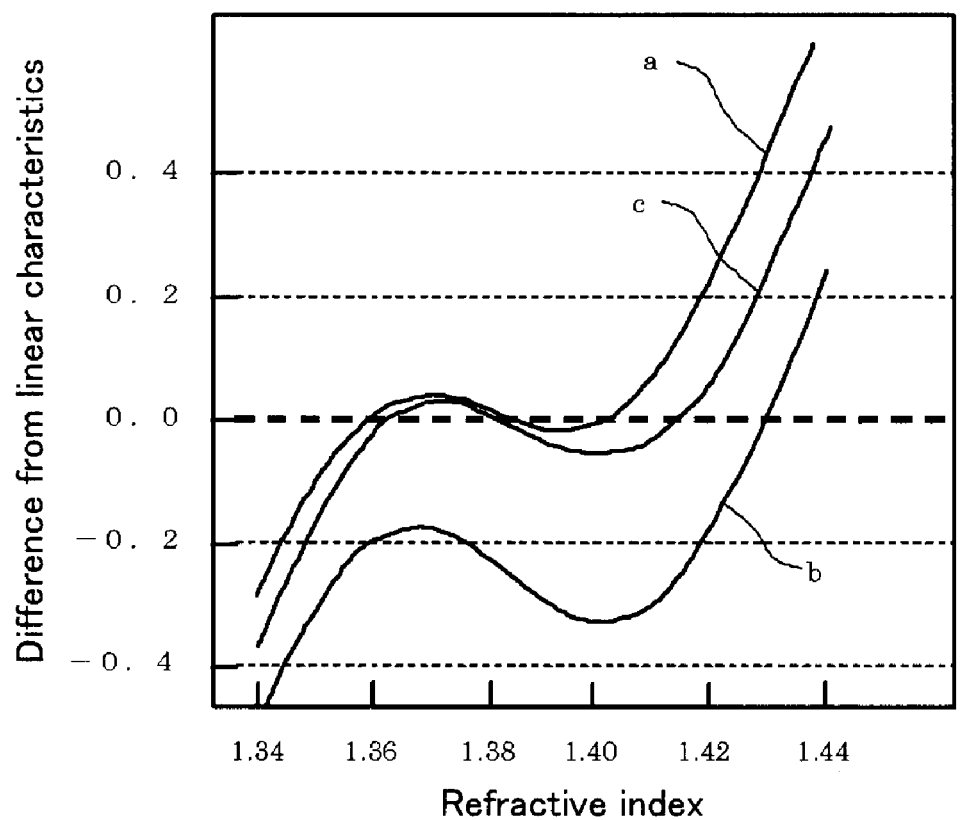
FIG. 12 is a graph representing difference from linear characteristics, of output from the optical fiber sensor according to Embodiment 1 of the present invention.
Figure 13:
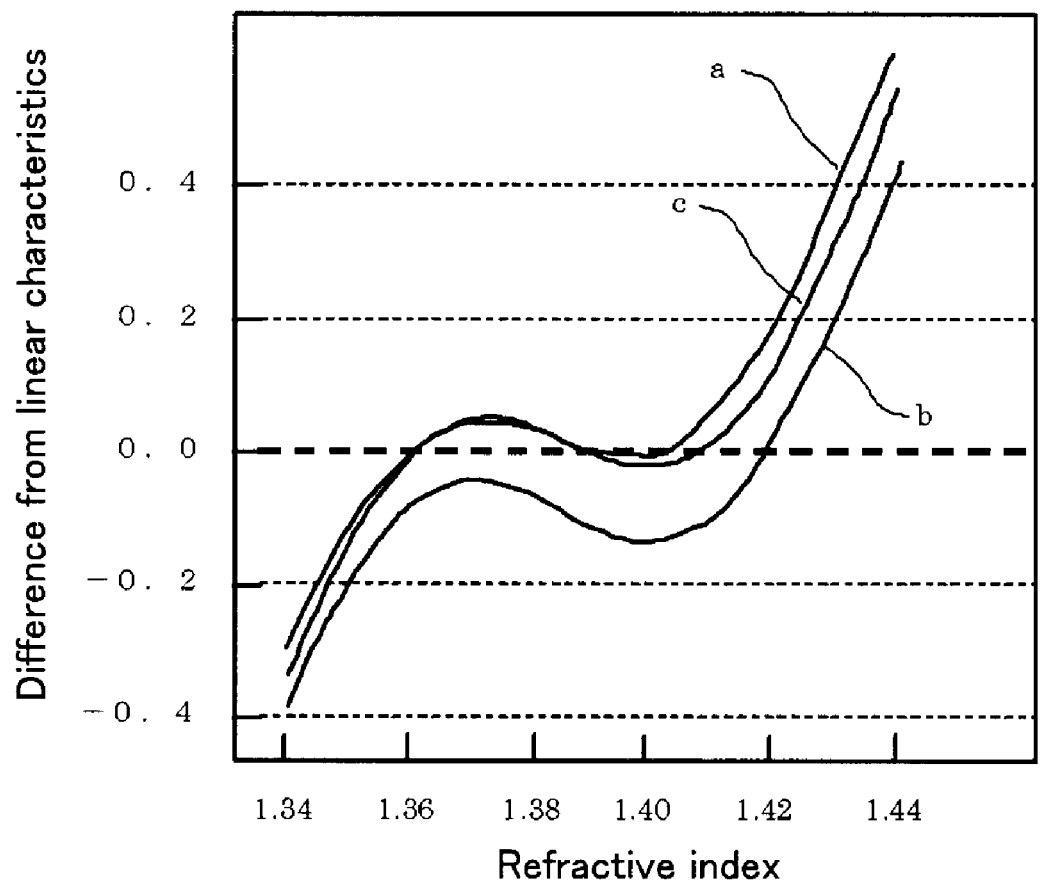
FIG. 13 is a graph representing difference from linear characteristics, of output from the optical fiber sensor according to Embodiment 1 of the present invention.
Figure 14:
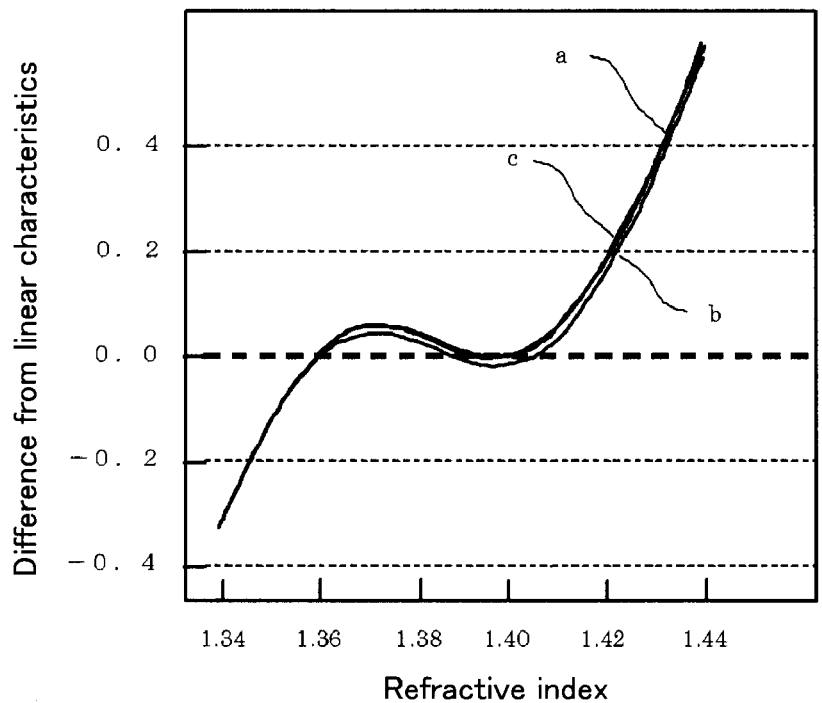
FIG. 14 is a graph representing difference from linear characteristics, of output from the optical fiber sensor according to Embodiment 1 of the present invention.

FIG. 12, FIG. 13, and FIG. 14 represent relative values of difference of the respective relationships represented in FIG. 9, FIG. 10, and FIG. 11 relative to a linear relationship that corresponds to a transmittance characteristic of the curve a (at the temperature of 27 degrees) in FIG. 9 assumed to be linear in a range from 1.36 to 1.40 of the refractive index. In these cases, symbols a, b and c also denote the difference values at the temperatures of 27 degrees, 48.5 degrees and 70 degrees, respectively.

First, comparing FIG. 12, FIG. 13, and FIG. 14 reveals that, when the period of the short-period gratings 10 is one kind as represented in FIG. 12, the differences from the linear relationship in the range from 1.36 to 1.40 of the refractive index are placed within plus/minus 0.05 (corresponding approximately to 5 percent) at the temperatures of 27 degrees and 70 degrees, while the differences becomes approximately plus/minus 0.15 (corresponding approximately to 15 percent) at the temperature of 48.5 degrees. This is because the degree of decrease in transmission light intensity becomes greater compared to the cases of the temperature being 27 degrees and 70 degrees.

In contrast, as represented in FIG. 13, when the periods of the short-period gratings 10 are three kinds, the differences from the linear relationship in the range from 1.36 to 1.40 of the refractive index are decreased approximately to be half, and when the periods of the short-period gratings 10 are five kinds, the differences from the linear relationship are further decreased. Such decrease in difference from the linear relationship caused by the period multiplexing is due to that the wavelength range width where the cladding propagation mode occurs increases with increasing the period multiplicity, so that ratio of the light intensity out of the range where the cladding propagation mode occurs can be decreased even when a shift of the light emission wavelength range of the light source 2 occurs by temperature. It is noted that, actually, effect of the spectrum shape of the light source is further included in the difference from the linear relationship.

Figure 15:
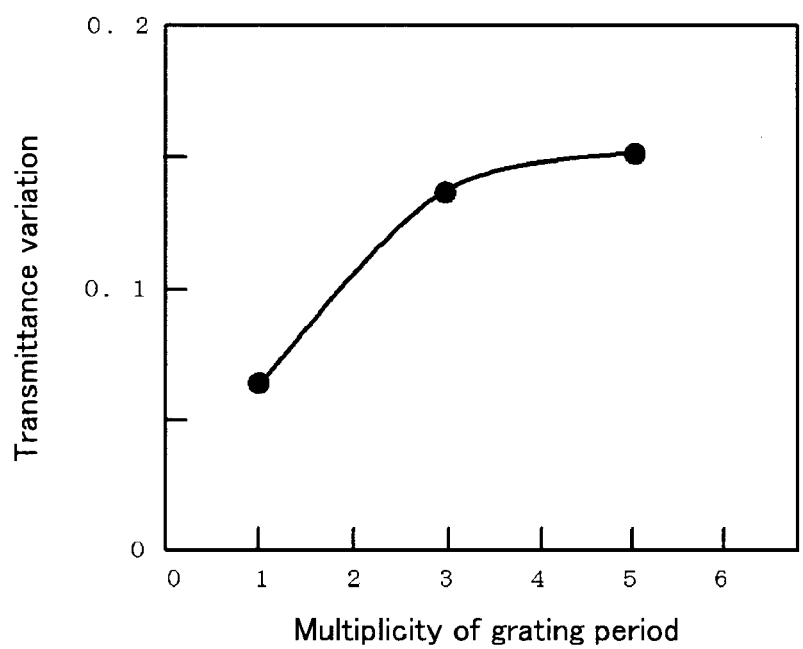
FIG. 15 is a relational graph representing transmittance variation against multiplicity of the grating period of the optical fiber sensor according to Embodiment 1 of the present invention.

FIG. 15 is a plotted graph against the multiplicity of the grating period, of the transmittance variations corresponding to the refractive-index variations in a range from 1.34 to 1.44 thereof represented in FIG. 9 to FIG. 11. As represented in FIG. 15, in comparison with the case of the period of the short-period gratings 10 being one kind, the amount of transmittance variation per refractive-index variation increases approximately up to double in both cases of three kinds and five kinds of periods. This means that the sensor becomes doubly more sensitive.

The increase of the transmittance variation amount by changing the multiplicity from the triple to the quintuple is small, which is because that the occurrence range of the cladding-propagation-mode in accordance with the triple multiplicity, almost meets the range of the light emission wavelength of the light source 2, so that the further added cladding-propagation-mode of double multiplicity at the both ends makes little contribution.

As described above, by causing cladding-propagation-mode transmission loss over a wavelength range equivalent to or wider than that of the light emission of the light source 2 using the short-period gratings 10 having the periods that are not limited to two kinds and may be three or more kinds, the sensor can be made most sensitive, and the temperature dependency of the sensor responsibility can also be smallest. That is, by causing cladding-propagation-mode transmission loss in a plurality of wavelength ranges within the wavelength range of the light emission of the light source 2, it is possible to increase the wavelength range where the cladding propagation mode occurs, for the total light amount emitted from the light source 2, whereby the light variation amount depending on increased/decreased degree of the thus-caused cladding-propagation-mode is made larger, resulting in improving detection sensitivity of the sensor.

Moreover, although the light-emission wavelength range of the light source 2 may be shifted in accordance with environmental temperature so that light intensity in the wavelength range under the cladding propagation mode is decreased, influence of the temperature dependency of the light-emission wavelength range of the light source can be reduced by extending the wavelength range where the cladding-propagation mode transmission loss occurs.

Figure 16:
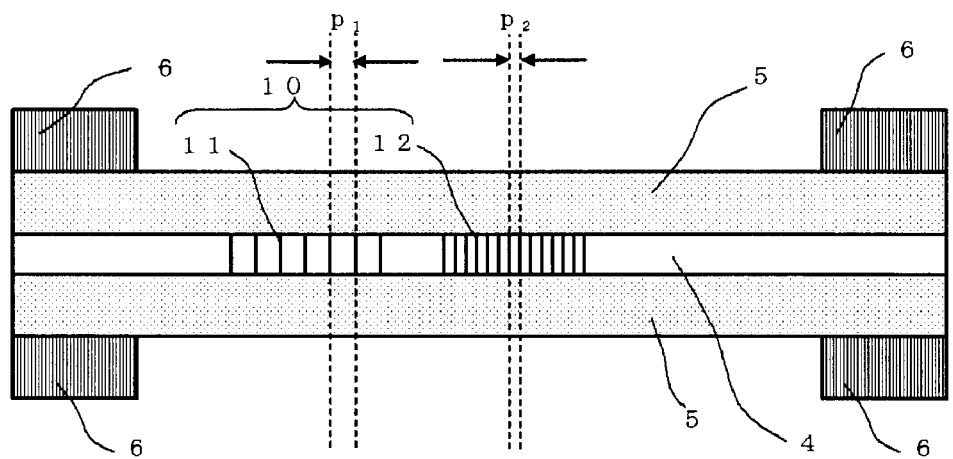
FIG. 16 is a cross-sectional schematic view of a region where short-period gratings of the optical fiber sensor according to Embodiment 1 of the present invention are formed.

Here, the optical fiber sensor according to this embodiment has been described as represented in FIG. 2, as a case in which the tilt angle of the first short-period grating 11 and the second short-period grating 12 provided in the core 4 of the optical fiber sensor is 8.6 degrees; however, the tilt angle of the first short-period grating 11 and the second short-period grating 12 each may be any degree, for example, zero degree as represented in FIG. 16 if the cladding propagation mode can be observed using, for example, a fiber grating whose core diameter is relatively small.

Figure 17:
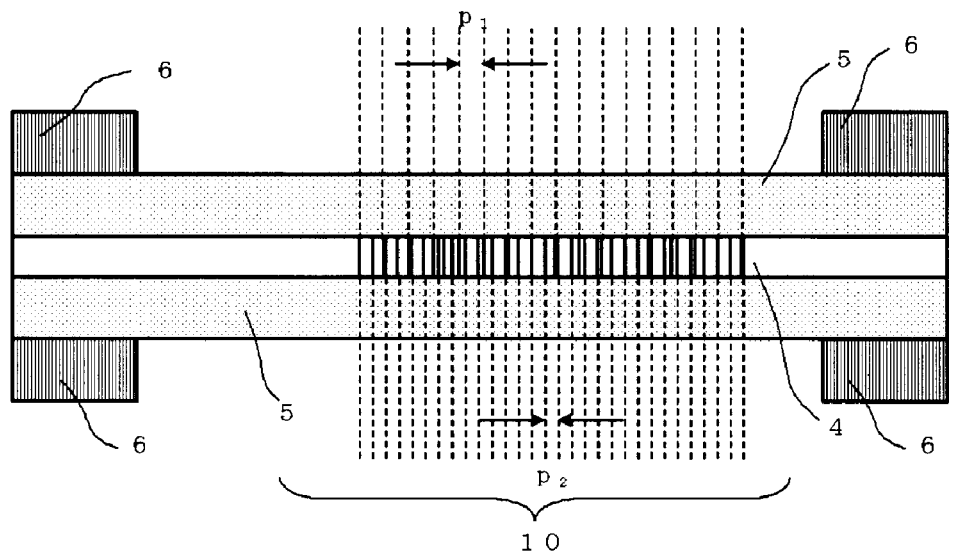
FIG. 17 is a cross-sectional schematic view of a region where short-period gratings of the optical fiber sensor according to Embodiment 1 of the present invention are formed.

Regions where the short-period gratings 10 having different periods are provided may be separated to each other as represented in FIG. 16; however, the regions may be overlapped as represented in FIG. 17. By providing the short-period gratings 10 having different periods to be overlapped to each other as represented in FIG. 17, the total length of the region of the short-period gratings 10 can be shortened, and the optical fiber sensor can be miniaturized.

Additionally, larger core diameter of the optical fiber 1 is preferable, because higher amount of light can be used. Generally, the core diameter of a single-mode optical fiber is smaller than approximately 10 micro-m, while that of a multi-mode optical fiber is larger than 10 micro-m. When a multi-mode optical fiber whose core diameter is 50 micro-m or 62.5 micro-m is used, a light emitting diode, even if having a small emission directionality, can easily be coupled as the light source 2 to the core 4 of the optical fiber 1, without using a lens for coupling. Therefore, the variation amount of the received light intensity can be larger relative to the amount of the detection light intensity and the variation of the refractive-index, so that an optical fiber sensor with higher detection sensitivity can be obtained by the use of the above combination.

Figure 18:
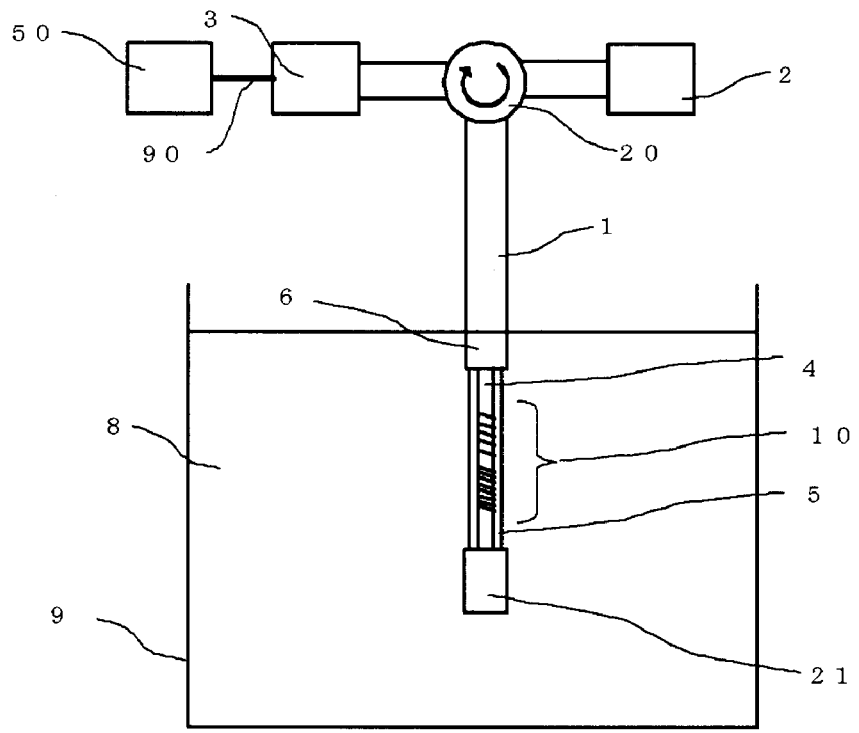
FIG. 18 is a schematic view explaining the optical fiber sensor according to Embodiment 1 of the present invention.

Shown in this embodiment is an example of the optical fiber sensor in which the light source 2 is arranged at one end of the optical fiber 1, the light receiving unit 3 is arranged at the other end, and the light receiving unit 3 detects light transmitted through the entire of the optical fiber 1 from the light source 2; however, as illustrated in FIG. 18, the refractive index can also be detected in a manner that light from the light source 2 is inputted through a circulator 20 into the optical fiber 1 at the end of which a reflection grating 21 is provided, and light intensity reflected from the region of the short-period gratings 10 is detected through the circulator 20 by the light receiving unit 3 provided on the same side of the optical fiber 1 as the light source 2. Here, instead of the circulator 20, another branch element such as a 3 dB optical fiber coupler can also be used. Moreover, instead of the reflection grating 21, another reflection element such as a metal mirror formed at the end face of the fiber can also be used.

According to the configuration of such a reflection-type sensor, because the transmission loss under cladding propagation mode can be caused to occur in both of the outward and homeward routes of the optical path, the measurement sensitivity can be improved, and the length of a portion, to be dipped in the target 8, of the optical fiber 1 can also be shortened. Moreover, because the measurement can be performed by inserting into the target to be measured, the fiber edge including no electrical-circuit unit, handling of the sensor can be simplified.

Here, as the light source 2, for example, a super-luminescent diode and a rare-earth-added optical-fiber light source other than the light-emitting diode can be used. As the light receiving unit 3, a light receiving device such as a photo-transistor other than the photo-diode may be used. As a material for the core 4 and the cladding 5, inorganic glass such as quartz glass or plastic material such as poly (methyl methacrylate) can be used, and as a material for the fiber jacket 6, fluorine group resin, nylon group resin, phenol group resin, epoxy group resin, and melamine group resin can be used.

Embodiment 2

The effect of the provision of the short-period gratings 10 having the periods different from each other has been explained in Embodiment 1. In this embodiment, an optical fiber sensor is explained that has a plurality of the short-period gratings 10 whose periods as well as tilt angles are different from each other.

First, a dependency of the refractive index of the target 8 against the tilt angle of the short-period grating 10 is explained. By changing the period of the short-period grating 10 as explained in Embodiment 1, the wavelength range where the transmission loss appears under cladding propagation mode can be shifted; however, the measurable range of refractive-index of the target 8 to be measured does not vary. In contrast, by changing the tilt angle of the short-period grating 10, it is possible to vary the measurable range of refractive-index of the target 8 to be measured, as well as to shift the wavelength range where the cladding-propagation-mode transmission loss appears.

Figure 19:
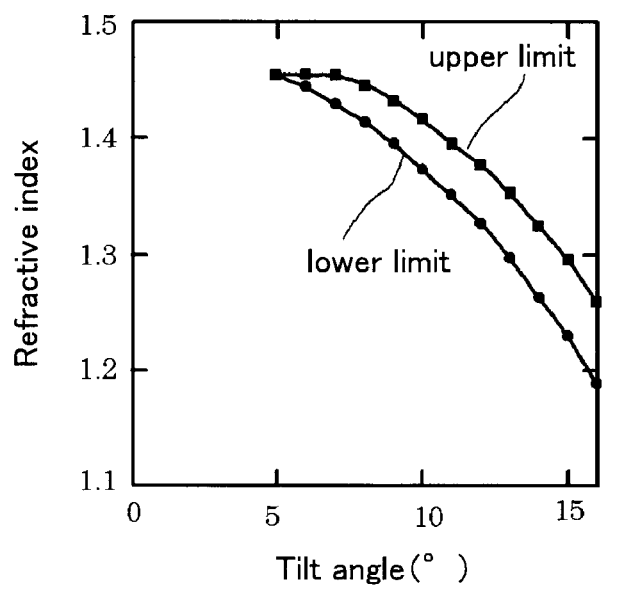
FIG. 19 is a schematic graph representing a measurement range of refractive indexes against tilt angles of short-period gratings according to Embodiment 2 of the present invention.

FIG. 19 represents a measurement range of the refractive index against the tilt angle with respect to the optical fiber sensor including the short-period gratings 10 having one kind of period, with a graded-index-type multi-mode optical fiber whose core diameter is 62.5 micro-m and an applied wavelength of approximately 880 nm. In FIG. 19, an upper limit and a lower limit of the refractive-index measurement range are represented. As represented in FIG. 19, by varying the tilt angle of the short-period grating 10, the refractive-index measurement range can be shifted. In this situation, the larger the absolute value of the tilt angle of the short-period grating 10, the more the wavelengths of the loss peaks under cladding-propagation-mode transmission shift to a shorter-wavelength side, and the smaller the measurable value of the refractive index. Moreover, the measurable range of the refractive index with respect to one kind of tilt angle is as smaller as approximately 0.03.

Figure 20:
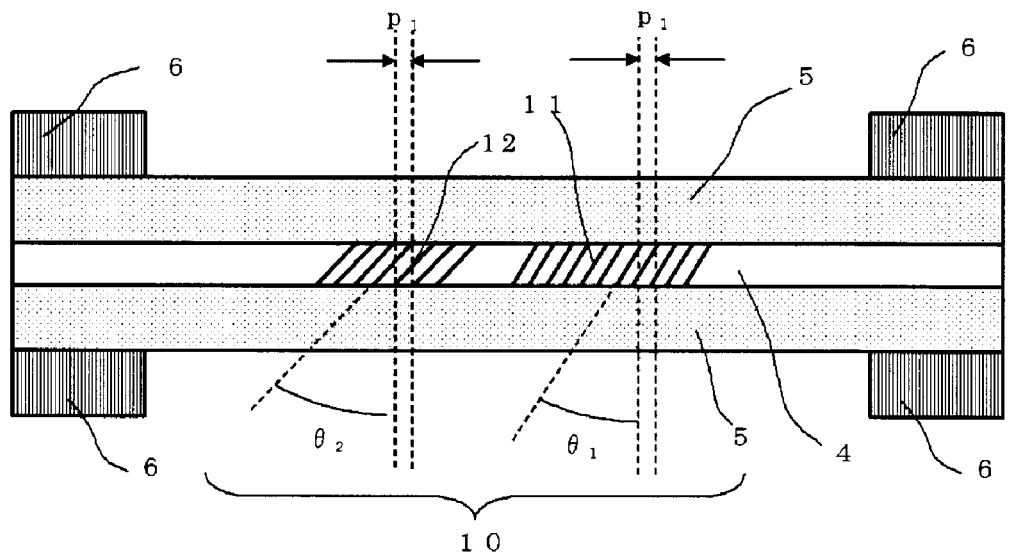
FIG. 20 is a schematic view for comparatively explaining a range where short-period gratings according to Embodiment 2 of the present invention are formed.

Therefore, by providing a plurality of tilt angles in the short-period gratings 10, a measurable range of the refractive-index can be extended. In the core 4 of the optical fiber sensor as illustrated in FIG. 20, the first short-period grating 11 and the second short-period grating 12 having the same period of p1 are provided to be separated. The first short-period grating 11 and the second short-period grating 12 are tilted at a first tilt angle theta-1 and a second tilt angle theta-2, respectively. The first tilt angle theta-1 and the second tilt angle theta-2 are values different from each other.

Figure 21:
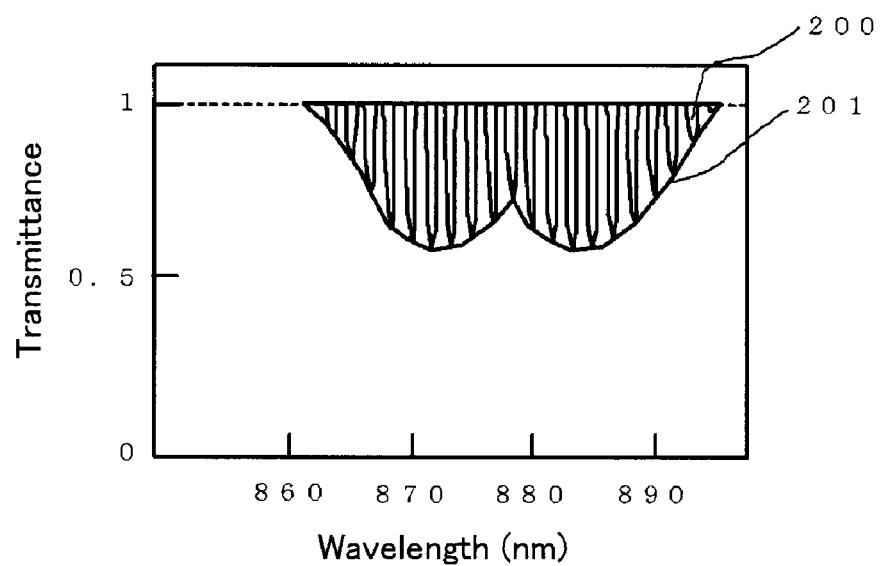
FIG. 21 is a schematic graph for comparatively explaining a transmittance of an optical fiber of an optical fiber sensor according to Embodiment 2 of the present invention.

In FIG. 21, transmittance characteristics of the optical fiber 1 having the short-period gratings 10, whose core diameter is 62.5 micro-m, period p1 is 0.3 micro-m, first tilt angle theta-1 is 8.6 degrees, and second tilt angle theta-2 is 10.0 degrees, configured as illustrated in FIG. 20, are schematically represented.

As illustrated in FIG. 21, in the optical fiber sensor configured as represented in FIG. 20, the cladding-propagation-mode transmission-loss peaks continuously appear in a relative wide range of approximately 25 nm from 865 nm to 890 nm. Additionally, the short-period gratings 10 have the two kinds of tilt angles, and the magnitude of the tilt angles have been suitably determined based on the dependency of the refractive-index measurement range to the tilt-angle as represented in FIG. 19, such that the sum of the measurement ranges is extended as much as possible, and the measurement ranges are partly overlapped to each other; therefore, the refractive index can be continuously detected in a relatively wide range of approximately 0.06. As described above, by forming the gratings having different tilt angles from each other, the refractive-index measurement range can be extended.

Figure 22:
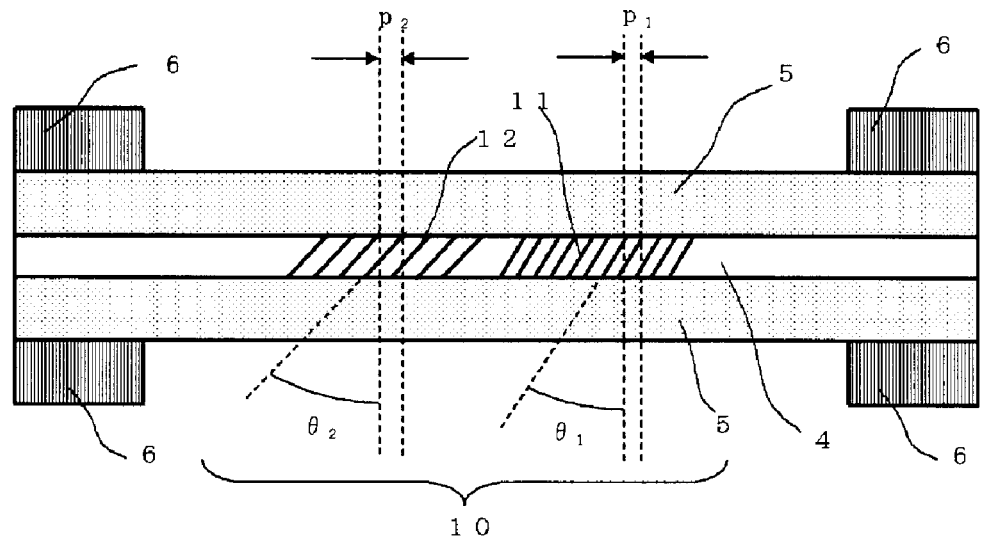
FIG. 22 is a cross-sectional schematic view of a region where short-period gratings according to Embodiment 2 of the present invention are formed.

FIG. 22 is a schematic view enlarging a region where the short-period gratings 10 of the optical fiber sensor according to this embodiment are formed. Because the other configuration is similar to that in Embodiment 1, the explanation is omitted. In the optical fiber sensor according to this embodiment, not only the periods but also the tilt angles of the first Bragg grating 11 and the second Bragg grating 12 are different from each other.

Figure 23:
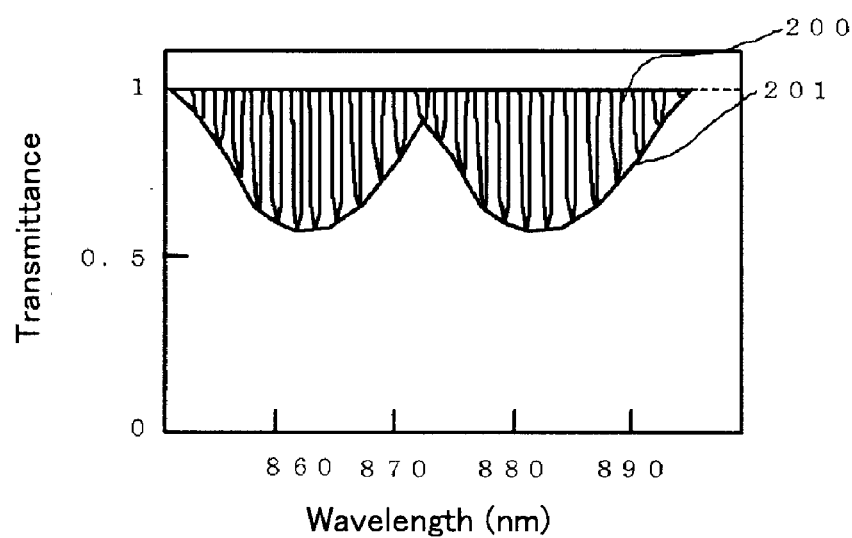
FIG. 23 is a schematic graph of a transmittance of the optical fiber of the optical fiber sensor according to Embodiment 2 of the present invention.

In FIG. 22, two kinds of short-period gratings 10 are provided so that the periods as well as the tilt angles of the first short-period grating 11 and the second short-period grating 12 are different from each other. In the core 4 of the optical fiber sensor according to this embodiment, the short-period gratings are provided to be separated to each other. When, in the optical fiber 1, the core diameter is 62.5 micro-m, the first period p1 is 0.3 micro-m, the second period p2 is 0.296 micro-m, the first tilt angle theta-1 is 8.6 degrees, and the second tilt angle theta-2 is 10.0 degrees, the transmission spectra of the optical fiber 1 are as represented in FIG. 23.

Also in the optical fiber sensor represented in FIG. 22, because the tilt angles are suitably set as explained in FIG. 21, the refractive index can be measured in the continuous refractive-index measurement range; moreover, because the wavelength range where the cladding-propagation-mode transmission-loss peaks of the optical fiber 1 occur is more extended compared to the case of using one kind of period, the sensitivity of the sensor, and the linearity and temperature dependency thereof to the refractive index can be improved based on a mechanism similar to that explained in Embodiment 1.

By adjusting the periods and the tilt angles as described above, the ratio of refractive-index measurement sensitivities between the short-period gratings, that are depending on their tilt angles, can be controlled. For example, by adjusting the tilt-angle dependent measurement sensitivities of the short-period gratings to be the same, the linearity of the output relative to the refractive index can be improved.

Moreover, similarly to Embodiment 1, due to shift of the light emission wavelength range of the light source 2 in accordance with environmental temperature, the light intensity in the wavelength range where the cladding-propagation-mode transmission-loss peaks occur may be decreased; however, by increasing the wavelength range where the cladding-propagation-mode transmission-loss peaks occur, influence of the temperature dependency of the light-emission wavelength range of the light source 2 can be reduced.

Here, the number of kinds of the short-period gratings 10 is not limited to the two kinds thereof represented in this embodiment, and three or more kinds of them may also be applied. An example of a case of four kinds of short-period gratings 10 will be explained with reference to FIG. 24, which is a schematic view enlarging a region where the short-period gratings 10 of the optical fiber are formed.

Figure 24:
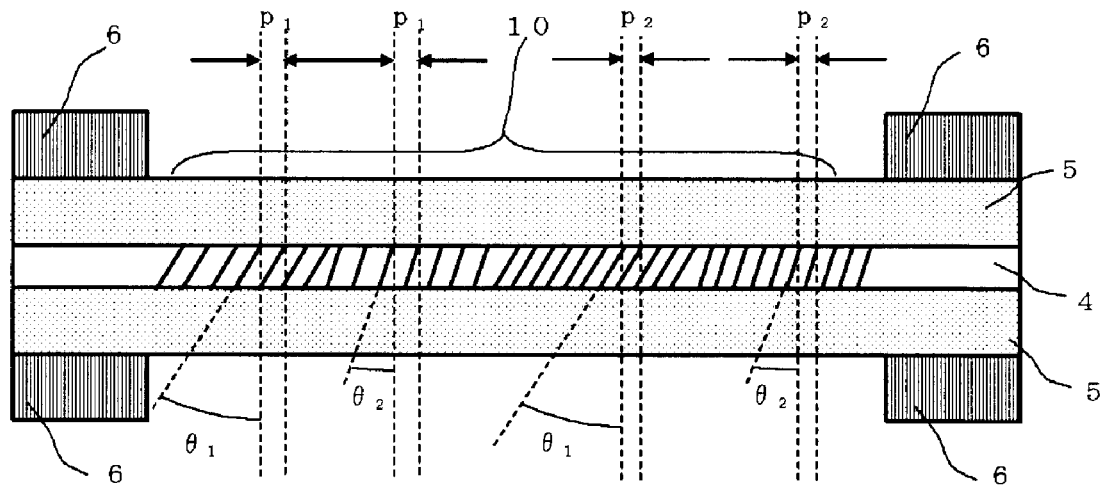
FIG. 24 is a cross-sectional schematic view of a region where short-period gratings of the optical fiber sensor according to Embodiment 2 of the present invention are formed.

As represented in FIG. 24, four kinds of short-period gratings having a first tilt angle theta-1 for the first period p1, a second tilt angle theta-2 for the first period p1, a first tilt angle theta-1 for the second period p2, and a second tilt angle theta-2 for the second period p2 are independently formed. In the core 4 of the optical fiber sensor according to this embodiment, the short-period gratings are provided to be separated from each other. The values of the first period p1 and the second period p2 are different from each other, and those of the first tilt angle theta-1 and the second tilt angle theta-2 are also different from each other.

Figure 25:
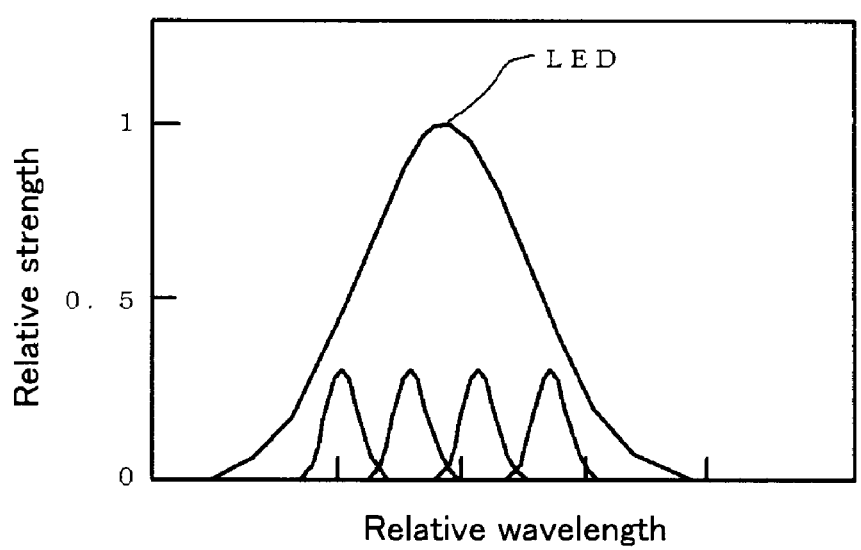
FIG. 25 is a schematic graph representing transmission loss spectra of the optical fiber and a light emission spectrum of the light source according to Embodiment 2 of the present invention.

Now, it is assumed that the short-period gratings having the first period p1 of 0.3 micro-m, the second period p2 of 0.292 micro-m, the first tilt angle theta-1 of 8.6 degrees, and the second tilt angle theta-2 of 10.0 degrees are formed with their respective lengths of 5 mm, in a total length range of 20 mm, in the core 4 of the multi-mode optical fiber having a cladding diameter of 125 micro-m, and a core diameter of 62.5 micro-m. In this case, because the transmittance of the optical fiber 1 can be schematically represented as in FIG. 25, and the tilt angles are suitably set as explained in FIG. 21 and FIG. 23, the sensor sensitivity, and the linearity and temperature dependency thereof to the refractive index can be improved.

Figure 26:
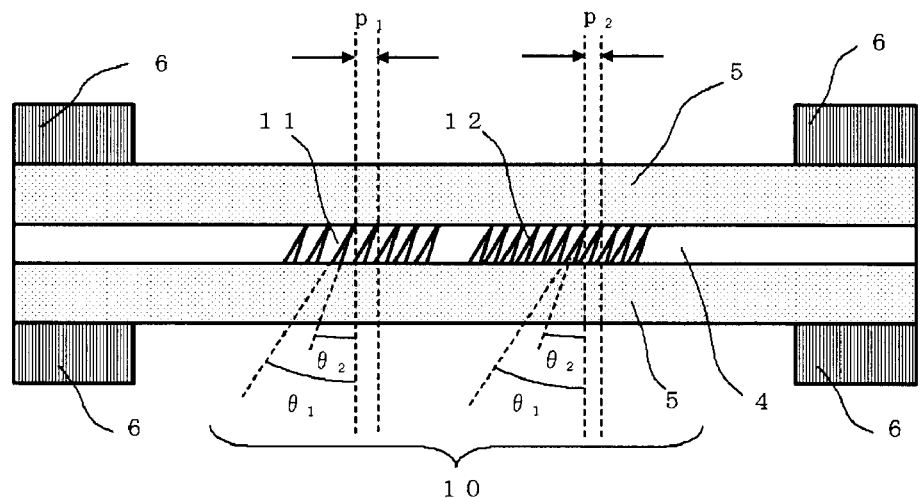
FIG. 26 is a cross-sectional schematic view of a region where short-period gratings of the optical fiber sensor according to Embodiment 2 of the present invention are formed.
Figure 27:
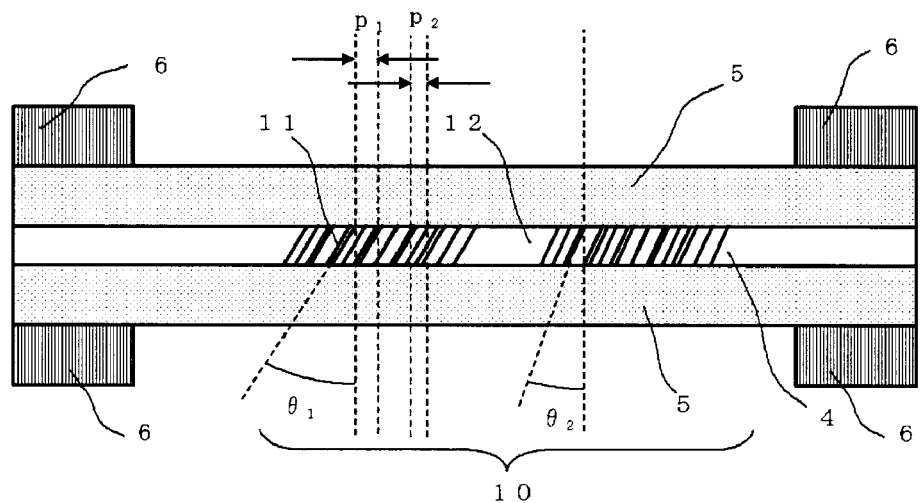
FIG. 27 is a cross-sectional schematic view of a region where short-period gratings of the optical fiber sensor according to Embodiment 2 of the present invention are formed.
Figure 28:
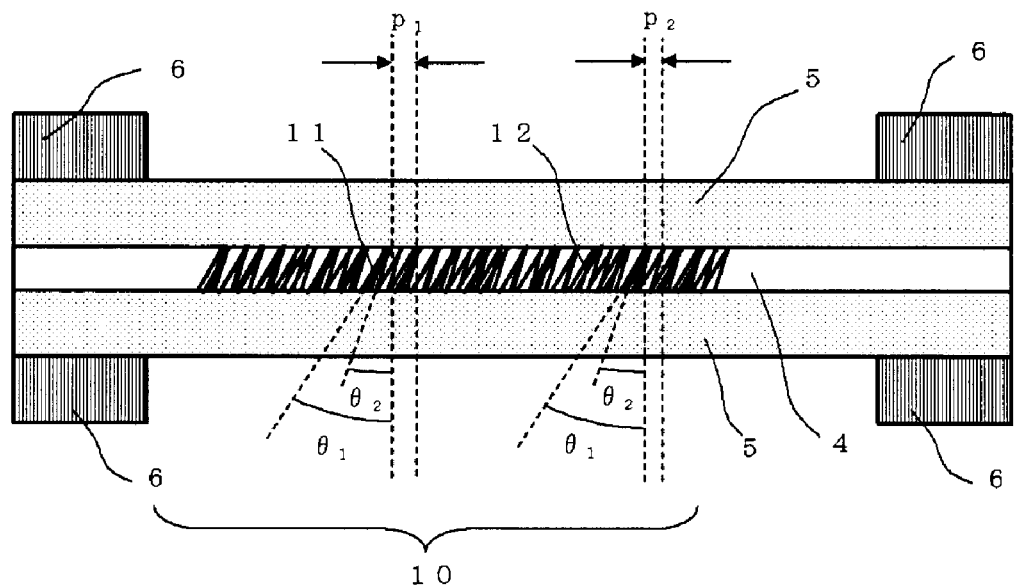
FIG. 28 is a cross-sectional schematic view of a region where short-period gratings of the optical fiber sensor according to Embodiment 2 of the present invention are formed.

Here, the short-period gratings 10 are not needed to be provided independently for each of the kinds, but, as represented in FIG. 26, the gratings whose periods are the same may be provided to be overlapped, or, as represented in FIG. 27, the gratings whose tilt angles are the same may also be provided to be overlapped. As represented in FIG. 28, all kinds of the above gratings may also be provided to be overlapped. As described above, by providing the different kinds of the short-period gratings to be overlapped, the total length of the short-period gratings can be shortened, and the sensor can be resultantly miniaturized.

By adjusting the periods and the tilt angles of the short-period gratings 10, respectively, in accordance with the range of the light-emission wavelength of LED as the light source 2, the sensitivity can be set at the maximum in a measurement required range of the refractive index. The four kinds of tilt angles of the short-period gratings are needed not to be classified into two angular sets such as 8.6 degrees and 10.0 degrees, but the tilt angle may be set at any intermediate value of these, that is corresponding to the refractive-index range where the measurement is to be performed. For example, the tilt angles may be different each other, such as at 8.2 degrees, 8.8 degrees, 9.6 degrees, and 10.2 degrees. Similarly, the periods are needed not to be classified into two periodical sets such as 0.3 micro-m and 0.292 micro-m, and the periods are suitably set so that a wavelength range where the cladding-propagation-mode transmission-loss peaks occur is adjusted to effectively utilize the emitted wavelength from the light source 2, such as at 0.3 micro-m, 0.299 micro-m, 0.292 micro-m, and 0.291 micro-m, for example.

Here, at around the upper and lower limits of a refractive-index measurement range for each of the tilt angles, the measurement sensitivity decreases compared to that in the approximate center of the measurement range, and therefore, the measurement sensitivity decreases in each region where the respective refractive-index measurement ranges are joined and where plural kinds of the tilt angles are straddling, and resultantly, linearity of the sensor characteristics may deteriorate. Therefore, by using short-period gratings having more than two kinds of tilt angles, such as four kinds, and by overlapping their measurement sensitivities in the region where the respective refractive-index measurement ranges are joined, the decrease of the measurement sensitivity in each region where the refractive-index measurement ranges are joined can be mitigated, and resultantly, the linearity of the sensor characteristics can be improved.

As described above, when the number of kinds of tilt angles of the short-period grating 10 are further increased from the two kinds, the wavelength range where the cladding-propagation-mode transmission-loss peaks occur can be further extended.

However, if the wavelength range where the cladding-propagation-mode transmission-loss peaks occur is extended more than necessary, detection sensitivity may be deteriorated. For example, it is assumed that the refractive-index range for measurement is 0.06, and the wavelength range where the cladding-propagation-mode transmission-loss peaks occur is extended to include other range than that corresponding to the refractive-index range within the light-emission wavelength range of the light source 2. Such extension of the wavelength range is effective only for increasing degree of light-amount that does not vary in its intensity even if the refractive index varies in a range where the measurement is to be performed, to thereby decrease the ratio of variation of light transmittance depending on the refractive index in the total light intensity, resulting in deteriorating the detection sensitivity.

Therefore, in addition to providing short-period gratings of plural kinds of the tilt angles corresponding to the intended refractive-index measurement range, it is preferable to extend according to the light-emission wavelength range of the light source 2, the wavelength range where the cladding-propagation-mode transmission-loss peaks occur, by a method of, for example, causing the short-period gratings to have plural kinds of periods as well.

As described above, in this embodiment, although the examples of the two kinds and the four kinds of short-period gratings 10 with different periods and tilt angles from each other have been represented, the number of kinds of short-period gratings 10 with different periods and tilt angles from each other may be more in so far as the detection sensitivity is improved.

Figure 29:
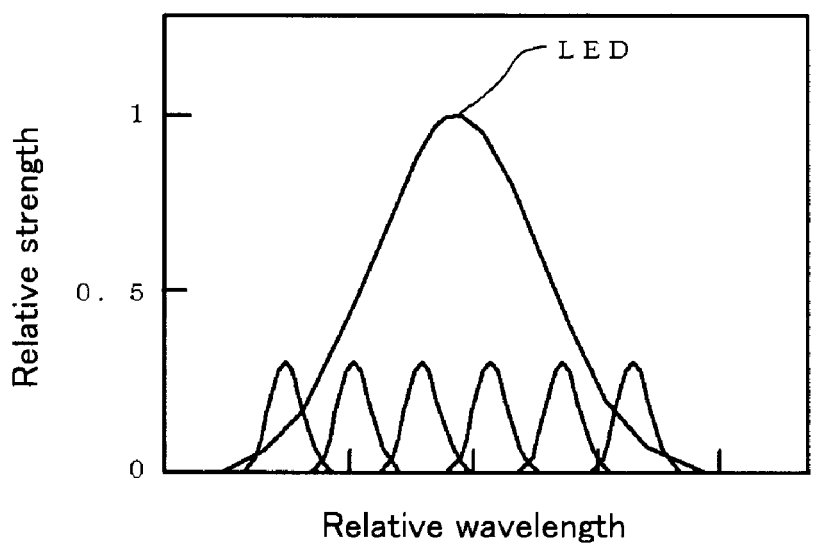
FIG. 29 is a schematic graph representing transmission loss spectra of the optical fiber and the emission spectrum of the light source according to Embodiment 2 of the present invention.

FIG. 29 represents a relationship between the emission spectrum of the LED as the light source 2 and transmission spectra of the optical fiber 1 having the multi-mode optical fiber core 4, whose cladding diameter is 125 micro-m, and core diameter is 62.5 micro-m, provided with totally six kinds of short-period gratings including three kinds, 0.284 micro-m, 0.292 micro-m and 0.3 micro-m of periods, and two kinds, 8.6 degrees and 10.0 degrees, of tilt angles. As represented in FIG. 29, by forming the wavelength ranges where the cladding-propagation-mode transmission-loss peaks occur corresponding to the plurality of periods and tilt angles, to occupy the entire region of the wavelength range of the light-source spectrum, the sensor can be set most sensitive, and the temperature dependency of the sensor responsibility can also be set at the least level.

Figure 30:
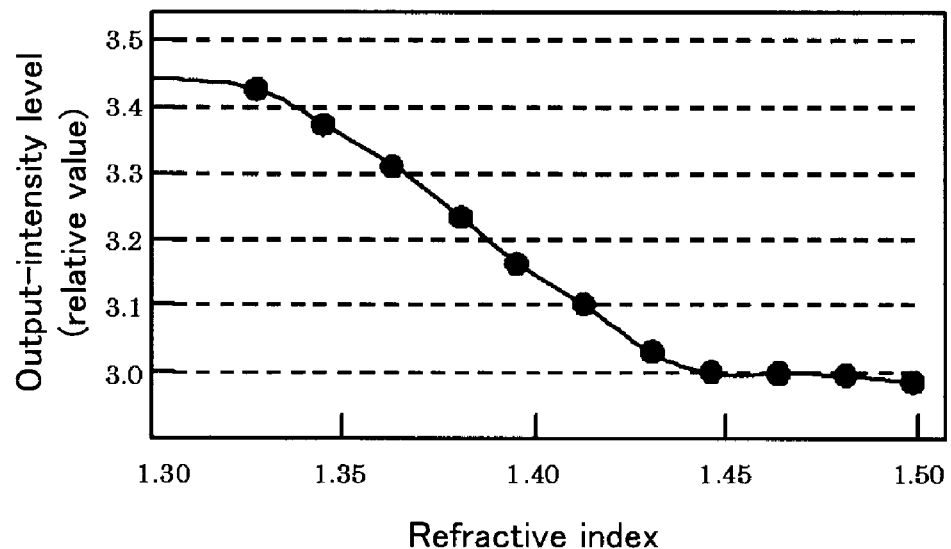
FIG. 30 is a schematic graph representing a relationship between refractive indexes and output-intensity levels of the optical fiber sensor according to Embodiment 2 of the present invention.

FIG. 30 represents relative output intensity of the sensor when liquid substances, each being the target 8, with different refractive indexes are measured using the optical fiber sensor configured as illustrated in FIG. 22 according to this embodiment. The liquid substances with different refractive indexes were prepared by changing the mixing ratio between methanol (n=1.329) and toluene (n=1.497). As illustrated in FIG. 28, according to the optical fiber sensor of this embodiment, the refractive index of the liquid having a value in the refractive-index range from 1.35 to 1.43 can be detected from the output of the sensor.

Figure 31:
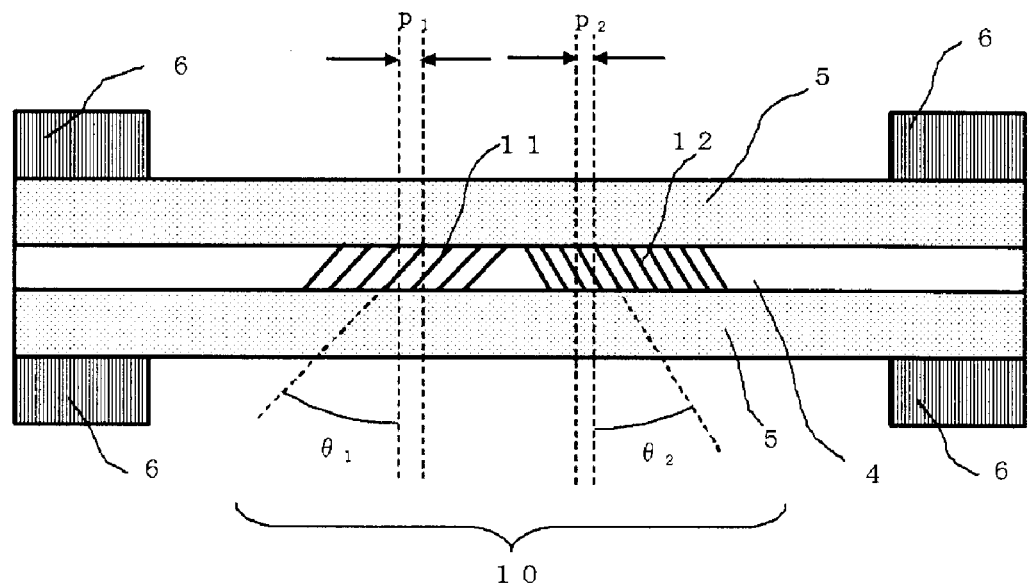
FIG. 31 is a cross-sectional schematic view of a region where short-period gratings of the optical fiber sensor according to Embodiment 2 of the present invention are formed.

Here, as described above, the example has been represented in which the plural tilt angles of the short-period gratings 10 are tilted in the same direction against the tilt angle of zero degree, that is, the angles are the same signed ones; however, the plurality of tilt angles of the short-period gratings 10 may be different signed ones from each other as illustrated in FIG. 31. As represented in FIG. 26-FIG. 28, when the regions where the different kinds of short-period gratings are provided are overlapped, by providing the tilt angles with their plus/minus signs interlaced to each other, the formation of the short-period gratings 10 become easier than the case of using tilt angles with one sign, because overlapping of refractive-index variation regions of the short-period grating 10 is smaller so that saturation of light is not easily occur.

Figure 32:
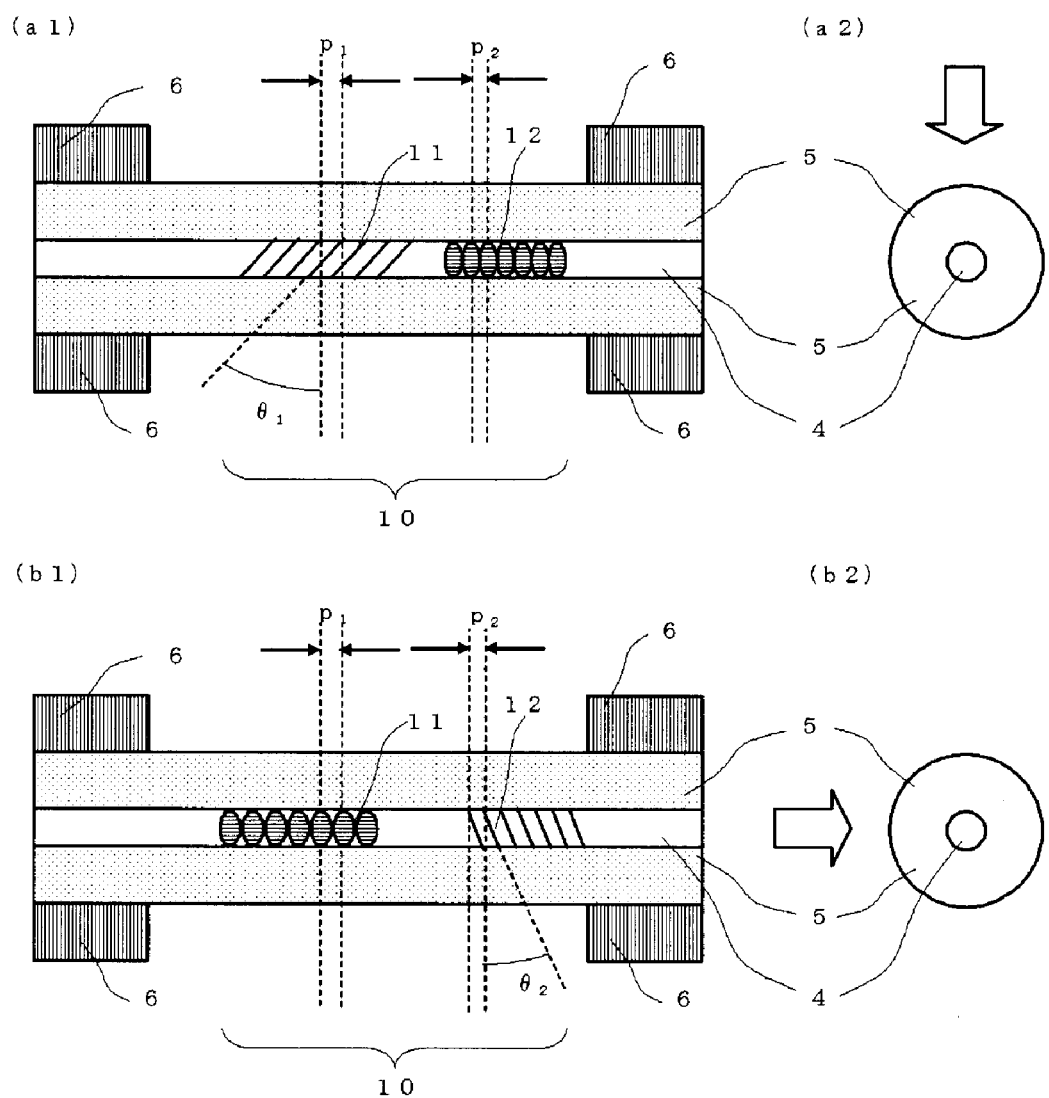
FIG. 32 is cross-sectional schematic views of regions where short-period gratings of the optical fiber sensor according to Embodiment 2 of the present invention are formed.
Figure 33:
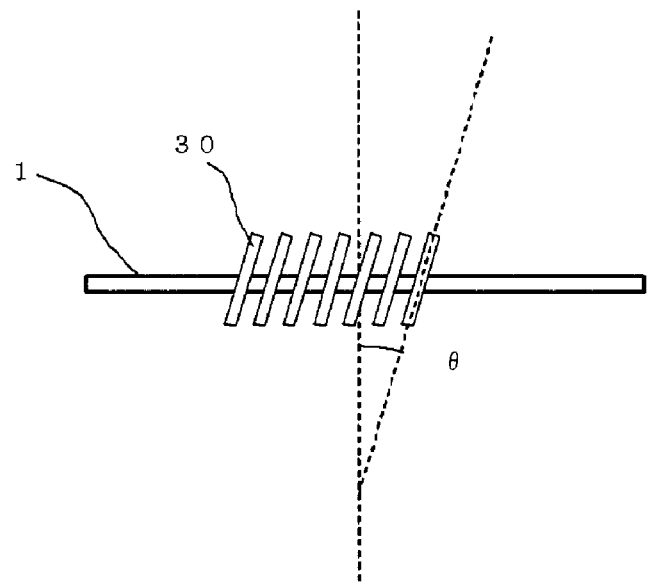
FIG. 33 is a schematic view representing a method of forming an optical fiber sensor according to Embodiment 3 of the present invention.

In the foregoing descriptions, although the plurality of tilts provided in the short-period gratings 10 have been explained as those viewed from the same direction, the plurality of the tilts of the short-period gratings 10 is not necessary to be those viewed from the same direction. The following explanation is made using FIG. 32 for a case in which a short-period grating is provided whose tilt is viewed from a different direction of 90 degrees rotation around the central axis of the optical fiber 1. FIG. 32($a1$) is a cross-sectional schematic view in which the optical fiber 1 is laterally viewed from an arrow direction of a diameter cross section represented in FIG. 32($a2$). While, FIG. 32($b1$) is a cross-sectional schematic view in which the optical fiber 1 is laterally viewed from an arrow direction of a diameter cross section represented in FIG. 32($b2$).

Also in this case, similar to that in FIG. 31, when the regions where the short-period gratings are provided are overlapped, the saturation of the light does not easily occur because the overlapping of the refractive-index variation regions of the short-period grating 10 is smaller, and thus, the short-period gratings 10 become easier to be formed.

Such an optical fiber 1 having the short-period gratings 10 can be formed by a method of changing the direction of the exposure light to the optical fiber 1 for its formation, for example, by rotating the optical fiber by a given angle around its central axis, for each time of the light exposure that is performed in plural times.

Embodiment 3

In the short-period grating 10 of the optical fiber sensor according to this embodiment, a region in which the refractive index is different from that of the core 4 is not planarly formed, but is curvedly provided. Hereinafter, such a short-period grating 10 is referred to as short-period grating 10 tilted with a continuously varying angle.

First, an explanation will be made for the optical fiber 1 represented in Embodiments 1, in which the tilt angle of the short-period grating 10 is uniform, that is, the region in which the refractive index is different from that of the core 4 is formed planarly.

The short-period grating 10 having a constant tilt angle is formed, for example, using periodical linear beams 30, having the wavelength of 266 nm, of the fourth harmonic wave from an Nd-YAG laser having the output power of 200 mW, by irradiating a multi-mode quartz optical fiber 1 whose fiber jacket 6 has been removed, with the linear beams 30 tilted by a predetermined angle to the central axis of the optical fiber 1. The optical fiber 1 is previously treated with high-pressure hydrogen (at 100 atm) for approximately two weeks. The periodical linear beams 30 can be obtained by irradiating the beam 30 through a phase mask, and the short-period grating 10 having an arbitrary tilt angle can be formed by controlling the tilt angle of the phase mask. Moreover, a phase mask may be used to form so that the short-period gratings 10 having the plural tilt angles can be formed by batch exposure.

Figure 34:
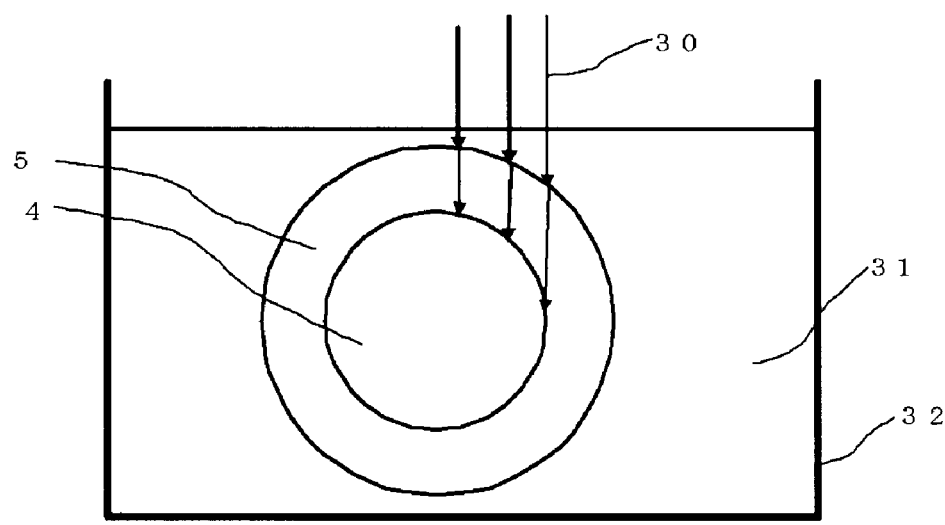
FIG. 34 is a schematic view for comparatively explaining a method of forming the optical fiber sensor according to Embodiment 3 of the present invention.

In this procedure, as represented in FIG. 34, when the laser is being emitted, the optical fiber 1 is placed in a medium such as water so that the refractive index of the cladding 5 of the optical fiber 1 and that of the medium outside the cladding are set to close values to each other. According to this technique, because the refraction ratio at the surface of the cladding 5 of the laser beam is reduced, the beams 30 are linearly incident on the core 4, and thus distribution of the tilt angles of the short-period grating 10 becomes narrower.

Here, in a case of the refractive index of the cladding 5 being close to that of the atmosphere, the beams 30 need not be emitted with disposing the optical fiber in a medium 31 as represented in FIG. 34. When the irradiation by the beams 30 are to be made in a medium, such a medium having no or less absorption of the beams 30 is selected. For example, because water is transparent at 266 nm of the wavelength as the fourth harmonic wave of the Nd-YAG laser, it is suitable for this wavelength of the beams 30.

Next, an explanation will be made for the short-period grating 10 tilted with a continuously varying angle, of the optical fiber 1 provided in the optical fiber sensor according to this embodiment. This short-period grating is formed by setting differently the refractive indexes of the core 5 of the optical fiber and the medium outside of the medium, although the short-period grating 10 having a constant tilt angle is formed by setting the refractive index of the cladding 5 of the optical fiber 1 and that of the medium outside the cladding to the values close to each other.

Figure 35:
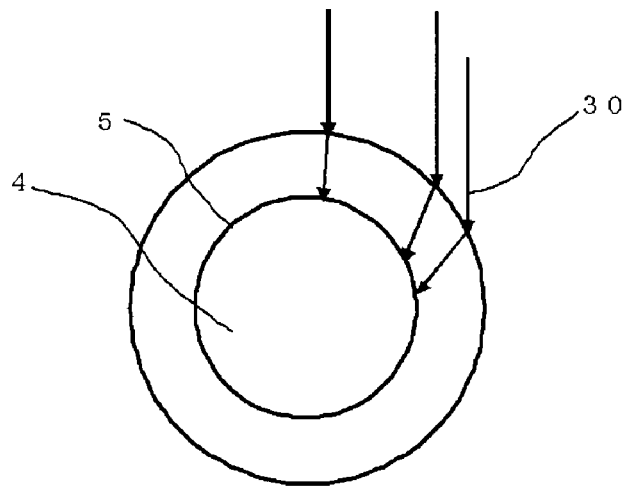
FIG. 35 is a schematic view representing a method of forming the optical fiber sensor according to Embodiment 3 of the present invention.

FIG. 35 is a schematic view representing optical paths, viewed from a cross-sectional direction of the optical fiber 1, of the beams 30 when the refractive index of the medium 31 outside the cladding 5 of the optical fiber 1 is smaller compared with that of the cladding. As represented in FIG. 35, because the refractive index of the medium 31 outside the cladding 5 is smaller than that of the cladding 5, the beams 30 are refracted at the interface between the cladding 5 and the medium 31 thereoutside. Therefore, the beam 30 going to reach the core 4 does not pass in a direction along the plane that the linear beam 30 forms outside the cladding 5, but the beam 30 passes along a curved plane. Because the refractive index of the core 4 varies for each of its regions through which the beams 30 pass, different refractive index regions to that of the core 4 is formed in a curved shape.

Figure 36:
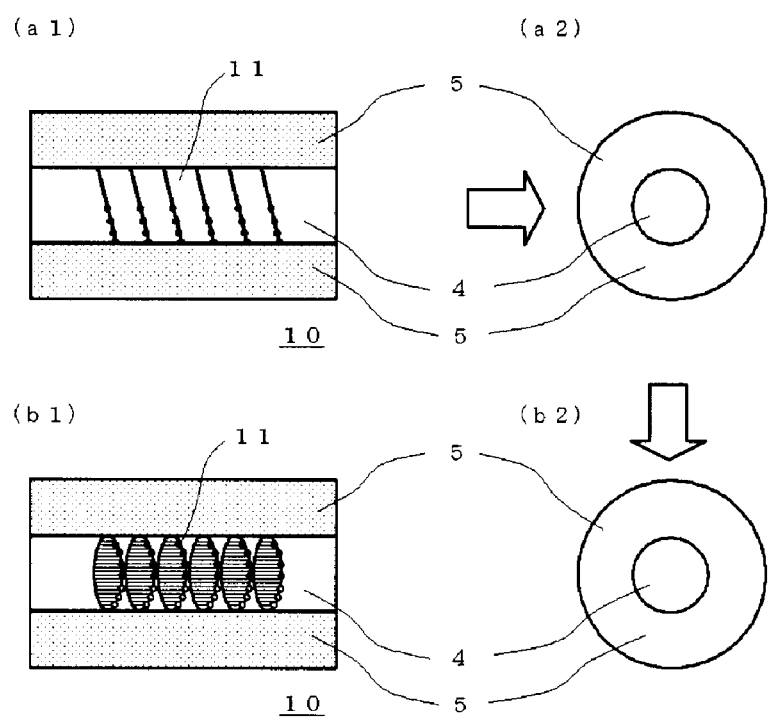
FIG. 36 is cross-sectional schematic views for comparatively explaining regions where short-period gratings of the optical fiber sensor according to Embodiment 3 of the present invention are formed.
Figure 37:
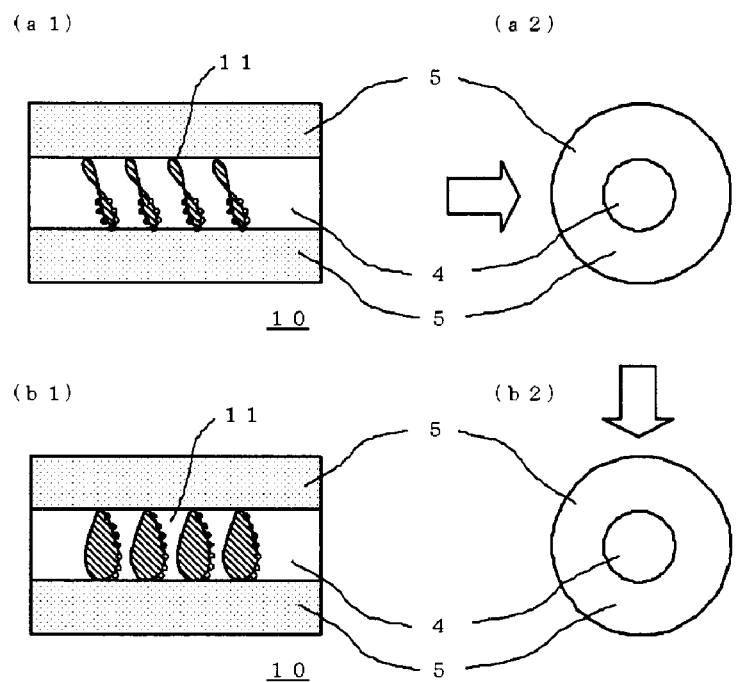
FIG. 37 is cross-sectional schematic views of regions where short-period gratings of the optical fiber sensor according to Embodiment 3 of the present invention are formed.

Such short-period gratings 10 formed in the cases of the refractive indexes of the cladding 5 and the medium thereoutside being approximately equal to and different from each other, will be explained in detail using FIG. 36 and FIG. 37, respectively. FIG. 36 directs to the case where the refractive indexes of the cladding 5 and the medium outside the cladding are approximately equal to each other, and shows a cross-sectional schematic view (a1) in which the short-period grating 10 is viewed from a direction (a2) laterally toward the optical fiber 1, and a cross-sectional schematic view (b1) in which the short-period grating 10 is viewed from another direction (b2) rotated from the above direction by 90 degrees around the central axis of the optical fiber 1, respectively. On the other side, FIG. 37 shows similar views in the case where the refractive indexes of the cladding 5 and the medium thereoutside are different from each other, which are schematic views enlarging a region where the short-period grating of the optical fiber sensor according to this embodiment is formed. Black circles and white circles in FIG. 36 and FIG. 37 represent positions of regions where the refractive indexes at the core/cladding interfaces are different from each other, and circular signs having the same color indicate the same position, which are indicators for explaining their spatial arrangement.

As represented in FIG. 36 and FIG. 37, the tilt angle in FIG. 36 is almost uniform independently of the positions inside the core 4, whereas the tilt angle in FIG. 37 continuously varies to form an angle distribution against the cross-sectional direction of the optical fiber 1, and increases with distance of the position inside the core 4 apart from its irradiated side of the beams 30. The tilt-angle distribution as represented in FIG. 37 is referred to as "tilted with a continuously varying angle" and here, a region where the refractive index is different from that of the core 4 is curvedly provided.

The short-period grating 10 represented in FIG. 37 can be regarded as overlapped short-period-gratings having tilt angles different from each other.

Figure 38:
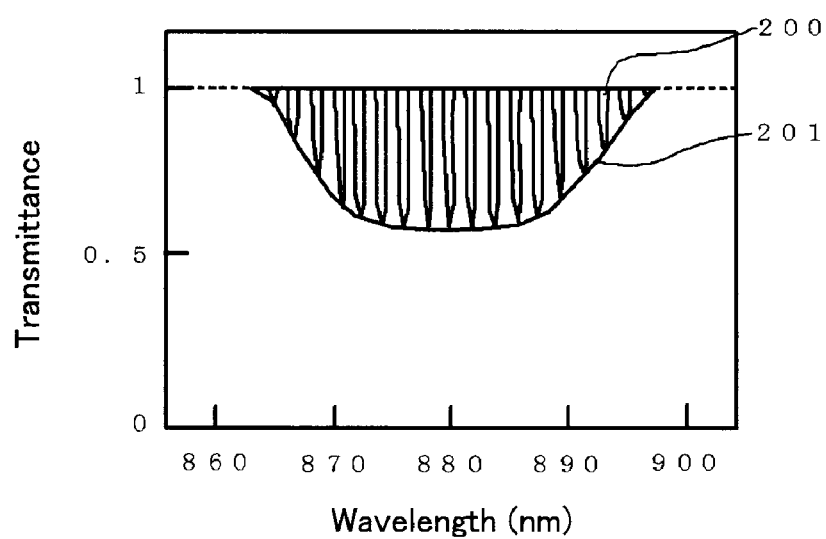
FIG. 38 is a schematic graph of a transmittance of an optical fiber of the optical fiber sensor according to Embodiment 2 of the present invention.

The transmittance of the optical fiber 1 including such a continuous-tilt-angle short-period grating 10 is schematically represented in FIG. 38. As represented in FIG. 38, because the wavelength range where the cladding-propagation-mode transmission-loss peaks occur is extended, the optical fiber sensor having high detection sensitivity and small temperature dependency can be obtained.

Here, in this embodiment, although the short-period grating 10 having one kind of period and a continuously tilted angle has been explained, the grating may have a plurality of periods similar to that in Embodiment 1. By adopting the plurality of periods, it is possible to increase the amount of light intensity variation relative to the increase/decrease of the occurrence degree of the transmission-loss-peaks under the cladding-propagation-mode, as similar to Embodiment 1.

Embodiment 4

In the short-period grating 10 of an optical fiber sensor according to this embodiment, the tilt angle gradually varies in a direction of the central axis 100 of the optical fiber 1. Such a short-period grating 10 is referred to as a short-period grating 10 whose tilt angle gradually varies.

Figure 39:
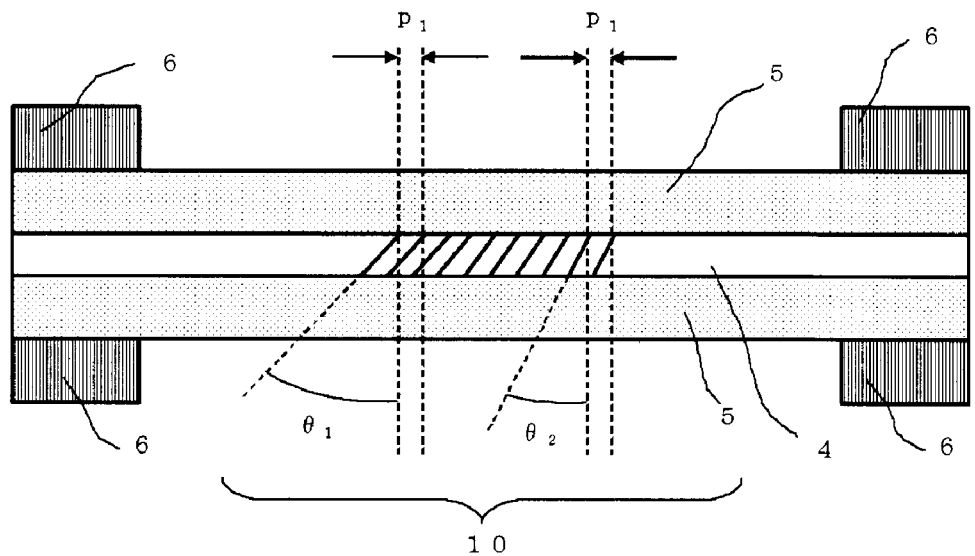
FIG. 39 is a cross-sectional schematic view of a region where short-period gratings of an optical fiber sensor according to Embodiment 4 of the present invention are formed.

FIG. 39 is a schematic view enlarging a region where the short-period grating 10 of the optical fiber sensor according to this embodiment is formed. Because the other configurations are similar to those in Embodiment 1, their explanation is omitted.

In FIG. 39, the short-period grating 10 having the first period p1 is provided in the core 4, in which the tilt angle gradually varies from theta-1 to theta-2 in the direction of the central axis 100 of the optical fiber 1.

Figure 40:
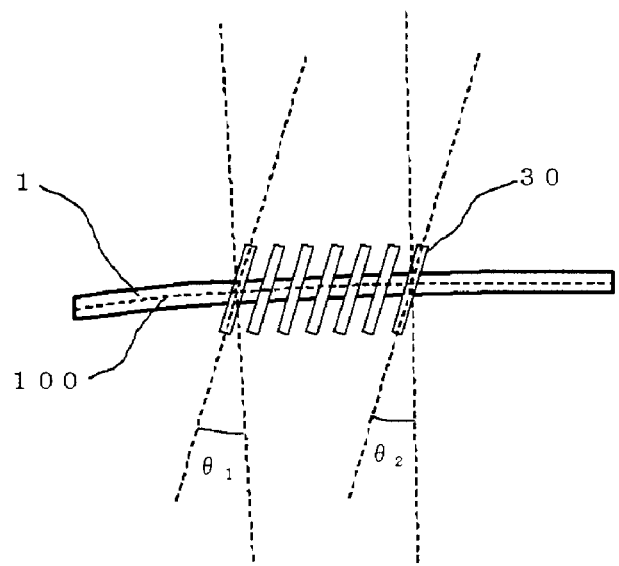
FIG. 40 is a schematic view representing a method of forming the optical fiber sensor according to Embodiment 4 of the present invention.

As represented in FIG. 40, the optical fiber 1 represented in FIG. 39 can be formed by irradiating an optical fiber 1 with the periodical linear beams 30, with the fiber being bent correspondingly to difference of the varying tilt angle.

According to the transmittance of such an optical fiber 1 having the short-period grating 10 whose tilt angle gradually varies, the wavelength range where the cladding-propagation-mode transmission-loss peaks occur is extended similarly to that in FIG. 38 of Embodiment 4, so that the optical fiber sensor whose detection sensitivity is relatively high and temperature dependency is relatively small can be obtained.

Embodiment 5

Although the optical fiber sensors according to Embodiments 1 to 3 are explained as used for measuring, for example, a refractive index of liquid, it is possible to accurately determine characteristics of the target from the measured refractive index and a measured temperature, by providing a mechanism for measuring the temperature of the target to be measured in addition to the optical fiber sensors according to Embodiments 1 to 3. In this embodiment, an optical fiber sensor for measuring characteristics of liquid, which is configured to combine a temperature-measurement mechanism, etc. with the optical fiber sensor according to Embodiment 1, will be explained.

Figure 41:
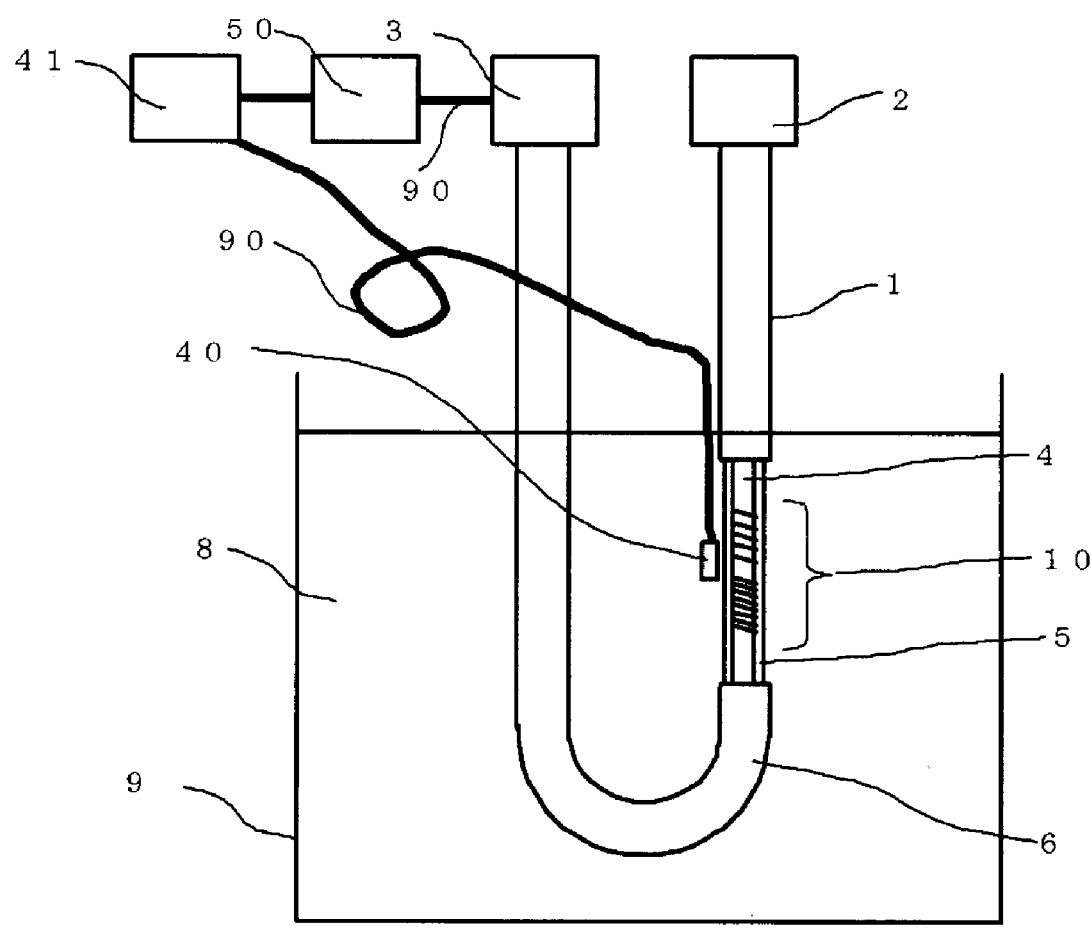
FIG. 41 is a schematic view explaining an optical fiber sensor according to Embodiment 5 of the present invention.

FIG. 41 is a schematic view explaining an optical fiber sensor that can more accurately measure a characteristic of the target 8. In FIG. 39, a thermometer 40 is provided at the proximity of the short-period gratings 10, and a characteristic calculation unit 41 is provided for receiving a signal through a signal line 80 from the thermometer 40. Another signal outputted from a refractive-index calculation unit 50 is also transmitted to the characteristic calculation unit 41 through a signal line 90. Because the other configurations are similar to those in Embodiment 1, their explanation is omitted.

As the refractive index of liquid as the target 8 generally has a temperature coefficient of approximately $-4 \times 10^{-4}$/K at around the room temperature, the characteristic of the target 8 whose temperature dependency of the refractive index of the target 8 is compensated, can be determined from the refractive index of the target 8 as the output of the target 8 and the output from the light receiving unit 3.

For example, in a case of ethanol mixed gasoline being used as the target 8, although the refractive index continuously varies depending on its mixing ratio, it is possible to determine accurately the mixing ratio of ethanol and gasoline using the optical fiber sensor according to this embodiment, by previously obtaining temperature dependency data of the target, that is, temperature calibration data, and by compensating effects of the measured temperature, based on the temperature calibration data.

As described above, according to the optical fiber sensor of this embodiment, even if a temperature dependency resides in the sensor characteristics, it is possible to more accurately determine the characteristic of the target by compensating the temperature dependency of the refractive index of the target 8 as well as that the temperature dependency of the sensor characteristics.

What is claimed is:
1. An optical fiber sensor comprising:
a light source;
an optical fiber including a core having a plurality of short-period gratings whose periods are different from each other, and a cladding for covering the core; and
a light receiving unit for detecting an intensity of light that has been inputted into the optical fiber from the light source and passed through the short-period gratings;
wherein at least one of the plurality of short-period gratings has a tilt angle.

2. An optical fiber sensor as recited in claim 1, wherein a first short-period grating and a second short-period grating included in the plurality of short-period gratings have respective tilt angles different from each other.

3. An optical fiber sensor as recited in claim 1,
wherein a first short-period grating and a second short-period grating included in the plurality of short-period gratings are provided so as to be overlapped with each other.

4. An optical fiber sensor as recited in claim 1, wherein a first short-period grating and a second short-period grating included in the plurality of short-period gratings are provided so as to be separated from each other.

5. An optical fiber sensor as recited in claim 2, wherein plus/minus signs of the tilt angles of the first short-period grating and the second short-period grating are inverse to each other.

6. An optical fiber sensor as recited in claim 2, wherein a central axis of the optical fiber, a refractive index varying axis of the first short-period grating, passing through the central axis of the optical fiber, and a refractive index varying axis of the second short-period grating, passing through the central axis, are not in the same plane.

7. An optical fiber sensor comprising
a light source;
an optical fiber including a core having a plurality of short-period gratings whose periods are different from each other, and a cladding for covering the core; and
a light receiving unit for detecting an intensity of light that has been inputted into the optical fiber from the light source and passed through the short-period gratings;
wherein transmission-loss wavelength ranges of the plurality of short-period gratings under a cladding propagation mode are continuous, and include an entire light-emission wavelength range of the light source.

8. An optical fiber sensor comprising:
a light source;
an optical fiber including a core having a short-period grating, tilted with a continuously varying angle and a region where the refractive index is different from that of the core being curvedly provided, and a cladding for covering the core; and
a light receiving unit for detecting an intensity of light that has been inputted into the optical fiber from the light source and passed through the short-period grating.

9. An optical fiber sensor comprising:
a light source;
an optical fiber including a core having a short-period grating whose tilt angle gradually varies in a direction of a central axis of the optical fiber, and a cladding for covering the core; and
a light receiving unit for detecting an intensity of light that has been inputted into the optical fiber from the light source and passed through the short-period grating.

10. An optical fiber sensor as recited in claim 1, wherein a refractive index of a measuring target contacting the cladding is measured based on the light intensity detected by the light receiving unit.

11. An optical fiber sensor as recited in claim 10, wherein characteristics of the target is determined based on the refractive index of the target.

12. An optical fiber sensor as recited in claim 8, wherein a refractive index of a measurement target contacting the cladding is measured based on the light intensity detected by the light receiving unit.

13. An optical fiber sensor as recited in claim 12, wherein characteristics of the target is determined based on the refractive index of the target.

14. An optical fiber sensor as recited in claim 9, wherein a refractive index of a measurement target contacting the cladding is measured based on the light intensity detected by the light receiving unit.

15. An optical fiber sensor as recited in claim 14, wherein characteristics of the target is determined based on the refractive index of the target.

* * * * *